US012090005B2

(12) United States Patent
Chauvette et al.

(10) Patent No.: US 12,090,005 B2
(45) Date of Patent: *Sep. 17, 2024

(54) POSITIONING APPARATUS FOR BIOMEDICAL USE

(71) Applicant: ConMed Corporation, Utica, NY (US)

(72) Inventors: Guillaume Chauvette, Victoriaville (CA); Charles Sévigny, Montreal (CA)

(73) Assignee: ConMed Corporation, Utica, NY (US)

( * ) Notice: Subject to any disclaimer, the term of this patent is extended or adjusted under 35 U.S.C. 154(b) by 302 days.

This patent is subject to a terminal disclaimer.

(21) Appl. No.: 16/587,275

(22) Filed: Sep. 30, 2019

(65) Prior Publication Data

US 2020/0022776 A1    Jan. 23, 2020

Related U.S. Application Data

(63) Continuation of application No. 15/357,115, filed on Nov. 21, 2016, now Pat. No. 10,426,570, which is a
(Continued)

(51) Int. Cl.
*A61G 13/00* (2006.01)
*A61B 90/14* (2016.01)
(Continued)

(52) U.S. Cl.
CPC .............. *A61B 90/50* (2016.02); *A61B 90/14* (2016.02); *A61F 5/3761* (2013.01);
(Continued)

(58) Field of Classification Search
CPC ...... A61F 5/3707; A61F 5/3792; A61F 5/055; A61F 5/05891; A61F 5/05883;
(Continued)

(56) References Cited

U.S. PATENT DOCUMENTS 2,652,221 A * 9/1953 Kampa .................. B60R 1/078
248/276.1
3,278,207 A * 10/1966 Barish .................... F16M 11/14
403/55
(Continued)

FOREIGN PATENT DOCUMENTS

WO    80/01366    7/1980
WO    98/49944    11/1998

OTHER PUBLICATIONS

CA Office Action, App. No. 3086577, dated Aug. 24, 2021, pp. 1-6.
(Continued)

*Primary Examiner* — Adam Baker
(74) *Attorney, Agent, or Firm* — Bond, Schoeneck & King, PLLC; Frederick J. M. Price

(57) ABSTRACT

A medical positioning apparatus including a telescopic member extending between first and second ends and having an adjustable length; a support member for receiving an object; a base member securable to a base; a first joint mechanism movably securing the support member to the first end of the telescopic member; a second joint mechanism including a housing with a top portion directly rotationally connected to the second end of the telescopic member, and at least one side portion directly rotationally connected to the base member and movably securing the base member to the second end of the telescopic member, a locking device operatively connected to the first and second joint mechanisms and the telescopic member, the locking device operable between a locked position and a released position; and a lock activation device to unlock the locking device biased in the locked position.

14 Claims, 14 Drawing Sheets

Related U.S. Application Data continuation of application No. 13/991,962, filed as application No. PCT/CA2011/001347 on Dec. 6, 2011, now Pat. No. 9,532,842.

(60) Provisional application No. 61/420,468, filed on Dec. 7, 2010.

(51) Int. Cl.
*A61B 90/50* (2016.01)
*A61F 5/37* (2006.01)
*A61G 13/12* (2006.01)

(52) U.S. Cl.
CPC ...... *A61G 13/128* (2013.01); *A61B 2090/508* (2016.02); *Y10T 403/32057* (2015.01)

(58) Field of Classification Search
CPC .............. A61G 13/128; A61G 13/1235; A61G 13/125; A61G 13/1245; A61G 7/1084; A61G 7/072; A61G 7/0506
USPC ............ 602/18, 17, 16, 12, 32, 36; 128/845, 128/846, 847
See application file for complete search history.

(56) References Cited

U.S. PATENT DOCUMENTS

| | | | | |
|---|---|---|---|---|
| 3,638,973 A * | 2/1972 | Poletti | .................... | A61B 17/02 285/306 |
| 5,284,313 A | 2/1994 | Hallgren | | |
| 6,220,556 B1 * | 4/2001 | Sohrt | .................... | F16C 11/106 403/56 |
| 6,435,186 B1 * | 8/2002 | Klemm | .................. | A61B 90/60 128/845 |
| 6,491,273 B2 * | 12/2002 | King | .................... | F16C 11/106 248/276.1 |
| 7,337,483 B2 | 3/2008 | Boucher et al. | | |
| 7,913,584 B2 * | 3/2011 | Arnold | ................. | B25J 19/0004 901/29 |
| 2002/0014567 A1 | 2/2002 | King et al. | | |
| 2007/0129634 A1 | 6/2007 | Hickey et al. | | |
| 2008/0203249 A1 * | 8/2008 | Priest | .................... | A61F 5/3761 248/118 |
| 2008/0203258 A1 | 8/2008 | Koenigstein | | |
| 2008/0214925 A1 | 9/2008 | Wilson et al. | | |
| 2009/0293884 A1 * | 12/2009 | DaSilva | ................. | A61G 13/12 128/845 |
| 2010/0018537 A1 * | 1/2010 | Soto | ........................ | A61G 13/12 128/845 |
| 2010/0204628 A1 * | 8/2010 | Ghajar | .................... | A61F 5/055 602/18 |

OTHER PUBLICATIONS

CA Office Action, App. No 3086577, dated May 6, 2022, pp. 1-4.
Article 94(3) Communication dated Mar. 20, 2024, Application No. EP 22 151 270.0, pp. 1-4.

* cited by examiner

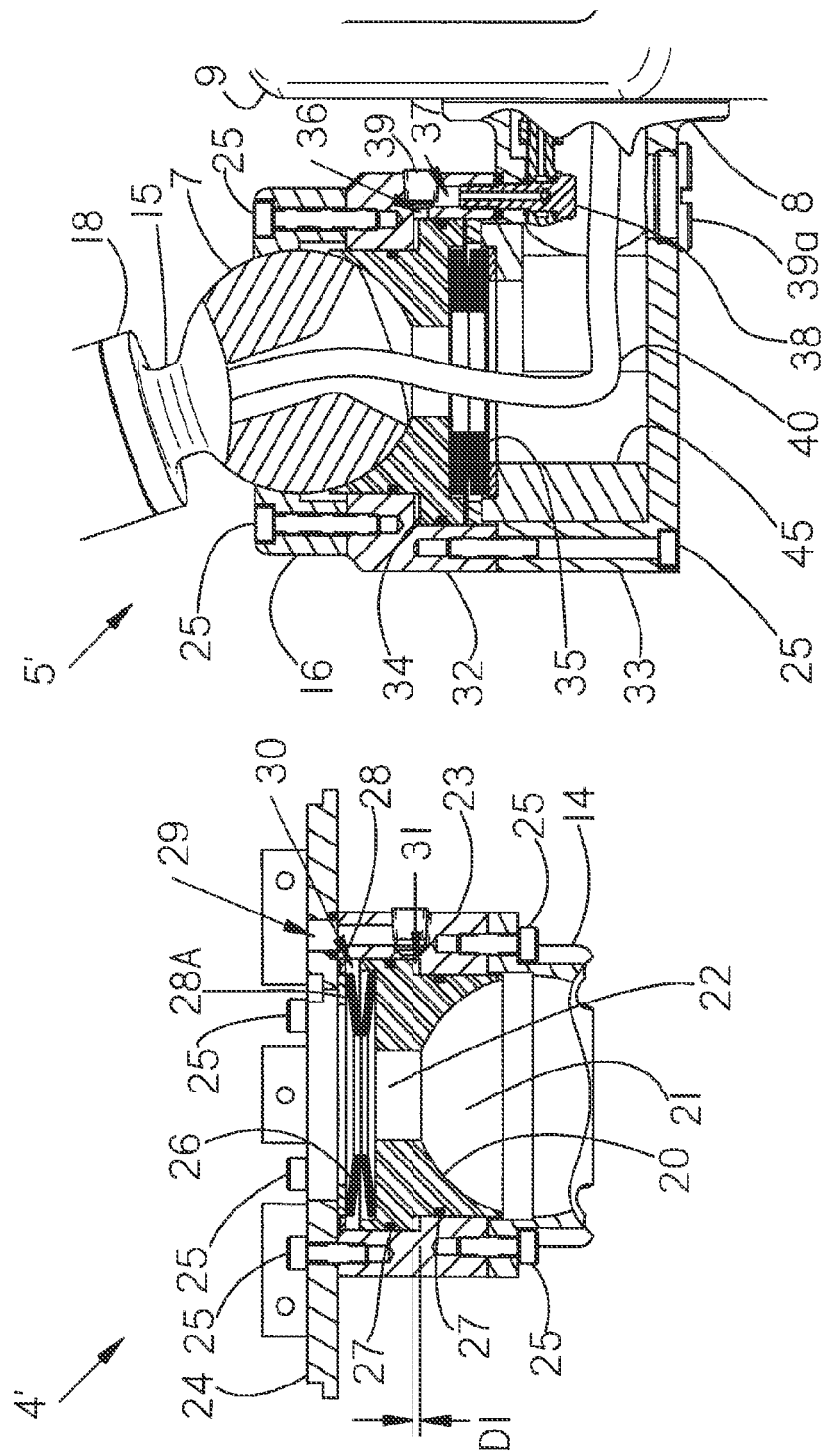

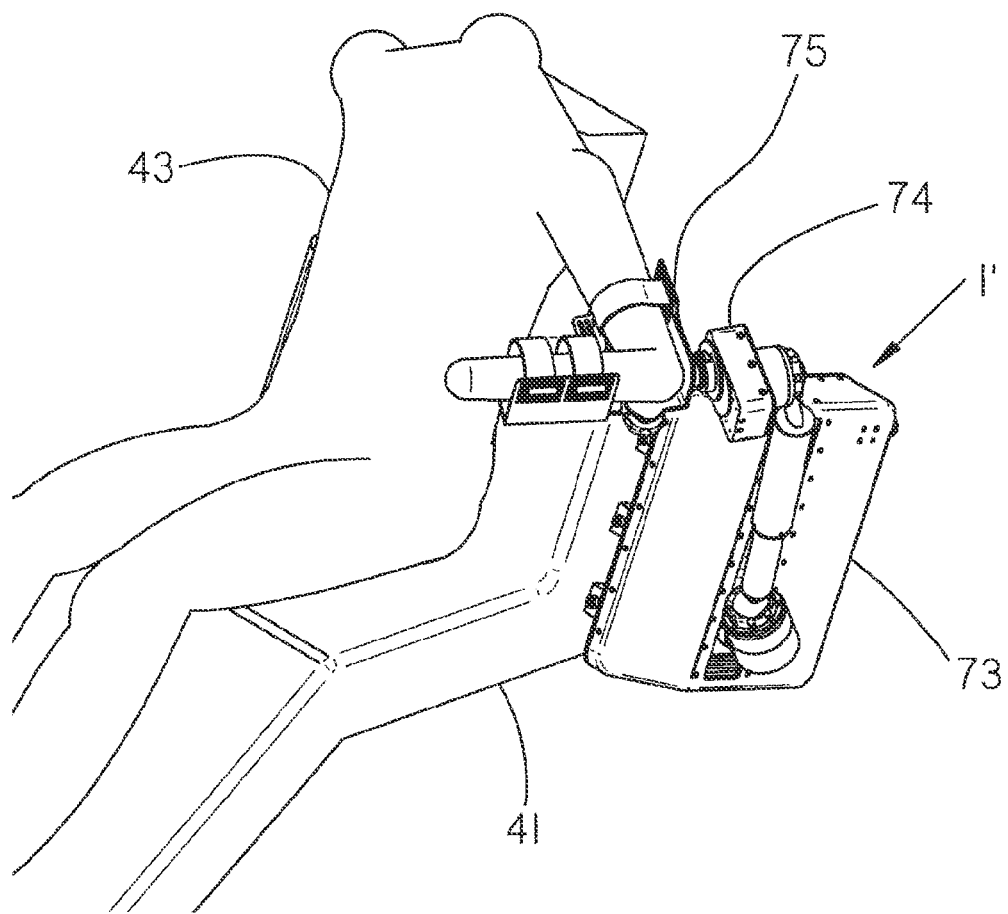
Figure II

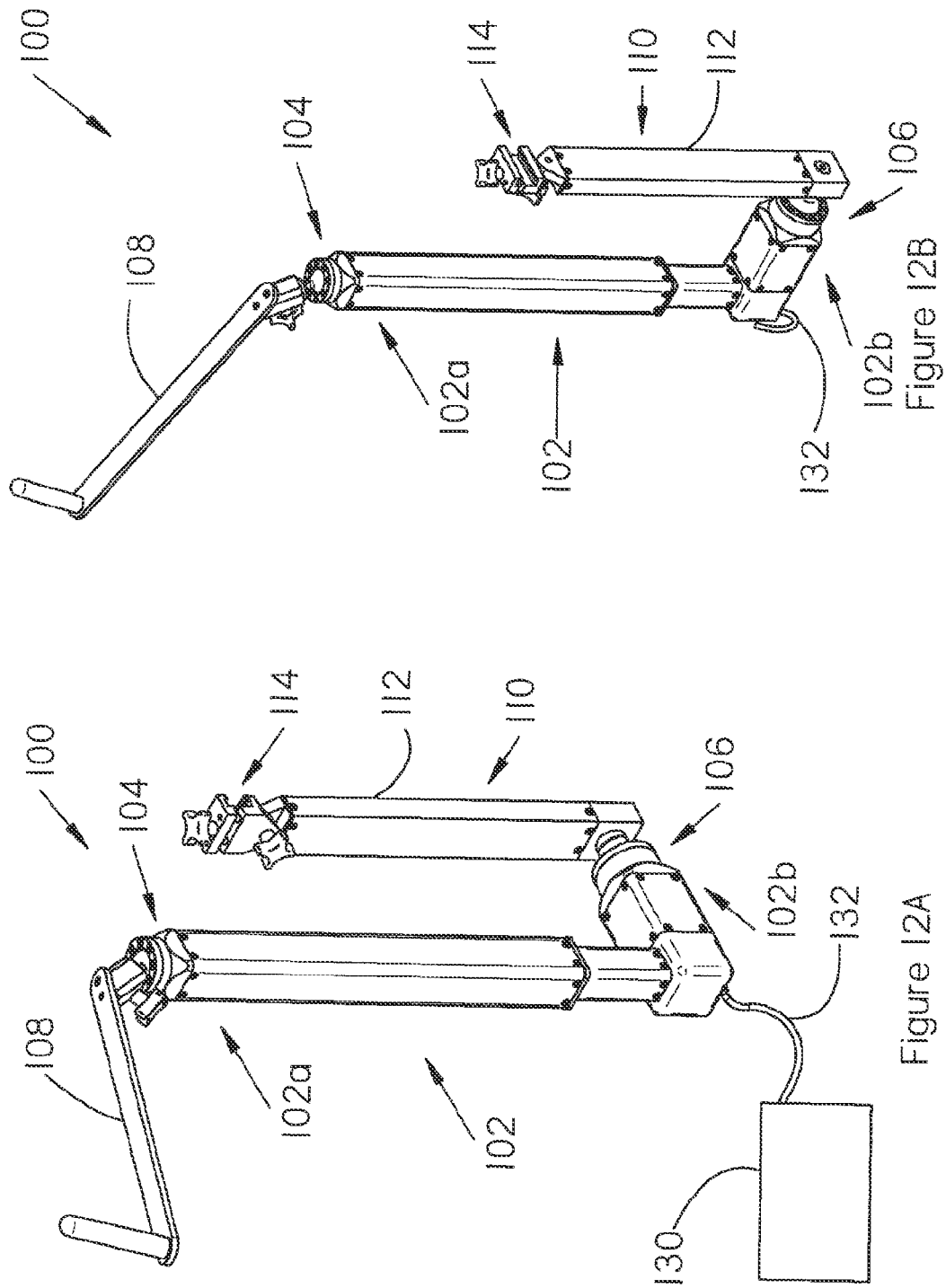

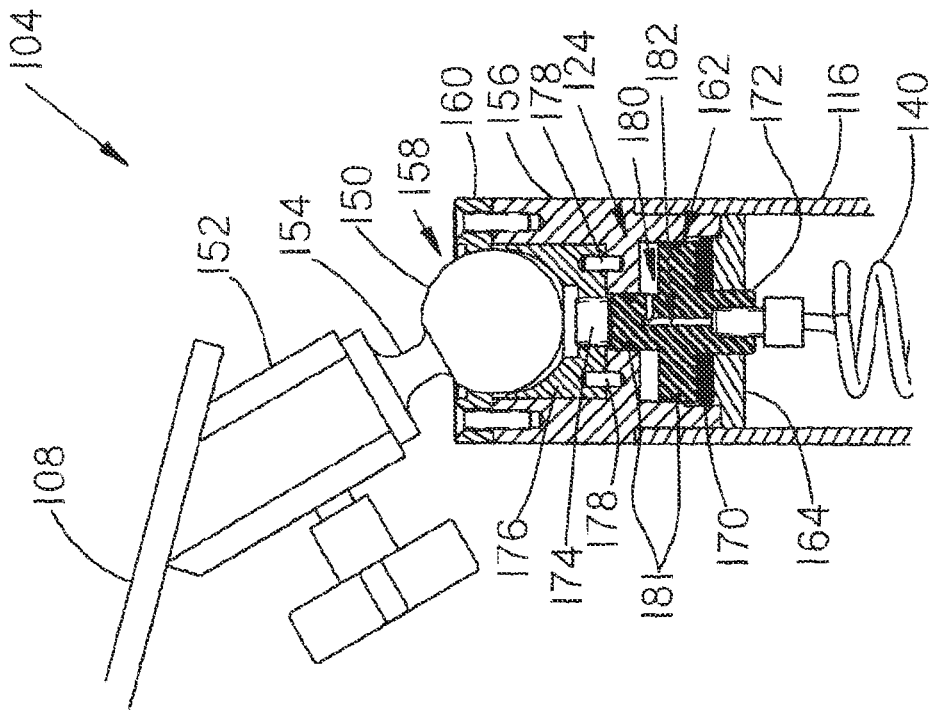
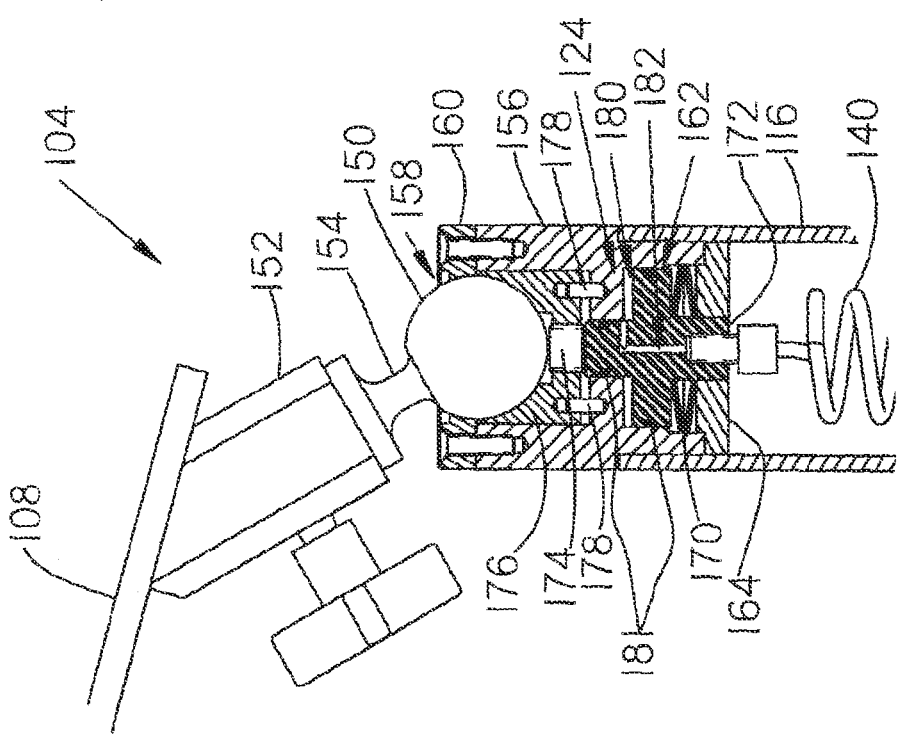

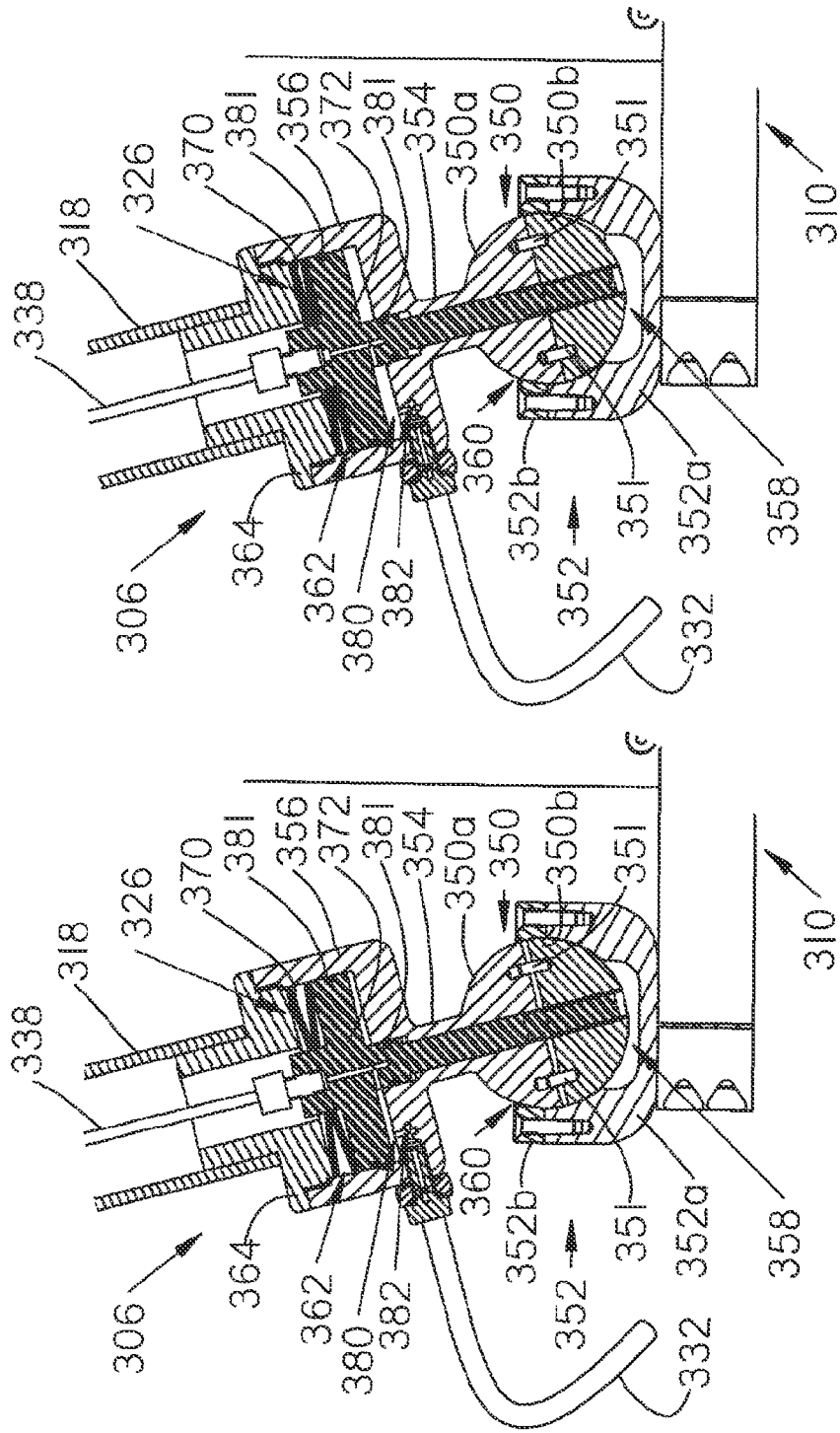

POSITIONING APPARATUS FOR BIOMEDICAL USE

CROSS REFERENCE TO RELATED APPLICATIONS

This application is a continuation of U.S. patent application Ser. No. 15/357,115, filed Nov. 21, 2016 which is a continuation of U.S. patent application Ser. No. 13/991,962, filed on Jun. 6, 2013, now U.S. Pat. No. 9,532,842 issued on Jan. 3, 2017, which is a U.S. National Phase Application pursuant to 35 U.S.C. § 371 of International Application No. PCT/CA2011/001347 filed on Dec. 6, 2011, which claims priority to U.S. Provisional Patent Application having Ser. No. 61/420,468, which was filed on Dec. 7, 2010 and is entitled "Positioning Apparatus for Biomedical and Robotic Uses", the contents of each are relied upon and incorporated herein by reference in their respective entireties.

FIELD OF THE INVENTION

The present disclosure generally relates to positioning apparatuses for holding and positioning objects, and more particularly to medical positioning apparatuses.

BACKGROUND OF THE INVENTION

Positioning apparatuses are currently used for multiple applications, including medical applications where they are used for maintaining limbs or other body parts, or holding surgical tools during surgical procedure for example. Positioning apparatuses may also have industrial applications where they may be used to hold tools or objects being manufactured.

Some medical positioning apparatuses comprise joints which are locked using hydraulic pressure and then released when this hydraulic pressure is removed. Such systems may require bulky hydraulic systems for maintaining a constant hydraulic pressure. Furthermore, such systems may not be fail-safe: in case of malfunction, for example when electrical power loss or a leakage causes a loss of hydraulic pressure, such positioning apparatuses may collapse.

Therefore, there is a need for an improved positioning apparatus.

SUMMARY OF THE INVENTION

According to a first broad aspect, there is provided a medical positioning apparatus for positioning and holding an object, including: a telescopic member extending between a first end and a second end and having an adjustable length; a support member for receiving the object; a base member securable to a base; a first joint mechanism movably securing the support member to the first end of the telescopic member; a second joint mechanism including a housing with a top portion directly rotationally connected to the second end of the telescopic member, a bottom portion opposite the top portion, and at least one side portion directly rotationally connected to the base member and movably securing the base member to the second end of the telescopic member, the first and second joint mechanisms each having at least two rotational degrees of freedom; a locking device operatively connected to the first and second joint mechanisms and the telescopic member, the locking device operable between a locked position in which the support member, the base member, and the telescopic member are lockingly interconnected together and the length of the telescopic member is fixed, and a released position in which the support and base members are free to pivotally move with respect to the telescopic member and the length of the telescopic member is adjustable, the locking device being passively biased in the locked position; and a lock activation device to unlock the locking device biased in the locked position in order to adjust the length of the telescopic member and a relative position of the support member, the base member, and the telescopic member.

In one embodiment, the locking device comprises a first, second, and third locking units operatively connected to the first joint mechanism, the second joint mechanism, and the telescopic member, respectively, and each passively biased in the locked position.

In one embodiment, each one of the first, second, and third locking units comprises an elastic member, a piston, and a brake pad operatively connected together, the elastic member being passively compressed when the first, second, and third locking units are in the locked position, and being further actively compressed when the first, second, and third locking units are in the released position upon activation of the lock activation device.

In one embodiment, the lock activation device is a pump fluidly connected to the first, second, and third locking units to define a closed-circuit containing a fluid in contact with the piston for the first, second, and third locking units, an activation of the pump causing an increase in a pressure of the fluid for further compressing the elastic member via the piston and unlocking the first, second, and third locking units.

The first and second joint mechanisms may each comprise a ball and a socket operatively connected together. In this case, the brake pad abuts the ball against the socket for preventing any relative motion between the ball and the socket when the first and second locking units are in the locked position, and is away/disengaged from the ball when the first and second locking units are in the released position.

In one embodiment, the first and second locking units are integrated into the socket of the first and second joint mechanisms, respectively.

In one embodiment, the ball comprises a first and a second hemispherical portions moveably connected together, the first hemispherical portion being fixedly secured to the telescopic member, the piston abutting the second hemispherical portion against the socket for preventing any relative motion between the ball and the socket when the first and second locking units are in the locked position, and the piston being away from the second hemispherical portion when the first and second locking units are in the released position.

In one embodiment, the telescopic member comprises a first elongated and hollow member and a second elongated member having a given end slidably engaged within the first elongated and hollow member, the third locking unit being secured at the given end of the second elongated member.

The brake pad of the third locking unit engages an internal surface of the first elongated and hollow member for fixing the length of the telescopic member when the third locking unit is in the locked position, the brake pad being away from the internal surface when the third locking unit is in the released position.

In one embodiment, the pump is a foot pump to be manually operable. In one embodiment, the elastic member is at least one Belleville spring.

In one embodiment, the lock activation device is adapted to substantially concurrently unlock the first, second, and third locking units.

In one embodiment, the lock activation device comprises one of a cable and push/pull/torsion rods.

In one embodiment, the support member comprises one of a limb support.

In one embodiment, the support member is a tool holder.

In one embodiment, the base member is securable to one of a bed, a chair, and a table.

According to a second broad aspect, there is provided a joint mechanism for a medical positioning apparatus, comprising: a first joint member; a second joint member including a housing with a top portion directly rotationally connectable to a telescopic member, a bottom portion opposite the top portion, and at least one side portion directly rotationally connectable to a base member, the second joint member movable with respect to the first joint member according to at least one degree of freedom; a locking device operatively connected to at least one of the first and second joint members, the locking device operable between a locked position in which the first and second joint members are lockingly interconnected together, and a released position in which the first and second joint members are free to move with respect to each other, the locking device being passively biased in the locked position and connectable to a lock activation device, the lock activation device for unlocking the locking device biased in the locked position in order to adjust a relative position of the first and second joint members.

In one embodiment, the locking device comprises an elastic member, a piston, and a brake pad operatively connected together, the elastic member being passively compressed when the locking device is in the locked position, and being actively further compressed when the locking device is in the released position upon activation of the lock activation device.

In one embodiment, the first joint member comprises a joint ball and the second joint member comprises a joint socket operatively connected to the joint ball, the brake pad abutting the joint ball against the joint socket for preventing any relative motion therebetween when the locking device is in the locked position, and the brake pad being away from the joint ball when the locking device in the released position.

In one embodiment, the first joint member is a first elongated and hollow member and the second joint member is a second elongated member having a given end slidably engaged within the first elongated and hollow member, the locking device being secured at the given end of the second elongated member, the brake pad of the locking device engaging an internal surface of the first elongated and hollow member for releasably securing the first and second elongated members together when the locking device is in the locked position, and the brake pad being away from the internal surface when the locking device is in the released position.

In the present description, an object should be understood as an inanimate object, such as a medical or surgical tool for example, or a living being or a part of living being, such as a human being limb for example.

The terms "resilient" and "elastic" are interchangeably used in the following description and used for characterizing a material capable reversible deformation.

The expressions "joint" or "joint mechanism" refers to a connection between two body members which allows relative movement between the two body members with one or more degrees of freedom between them.

BRIEF DESCRIPTION OF THE DRAWINGS

Further features and advantages of the present invention will become apparent from the following detailed description, taken in combination with the appended drawings, in which:

FIG. 5 is a side cutaway view of the movable spherical joint mechanism of FIG. 4 in locked position;

FIG. 6 is a side cutaway view of a movable spherical joint mechanism attached to a telescopic arm and to a base, in accordance with a first embodiment;

FIG. 11 is a use of the positioning apparatus of FIG. 3 as a limb support, showing further showing an axial traction device;

FIGS. 12A and 12B illustrate a positioning apparatus, in accordance with another embodiment;

FIGS. 14A and 14B illustrate a cross-sectional view of an upper joint mechanism of the positioning apparatus of FIG. 12A, in a locked and released position, respectively;

FIGS. 18A and 18B illustrate a cross-sectional view of a lower joint mechanism of the positioning apparatus of FIG. 17, in a locked and released position, respectively.

It will be noted that throughout the appended drawings, like features are identified by like reference numerals.

DETAILED DESCRIPTION

Figure 2:
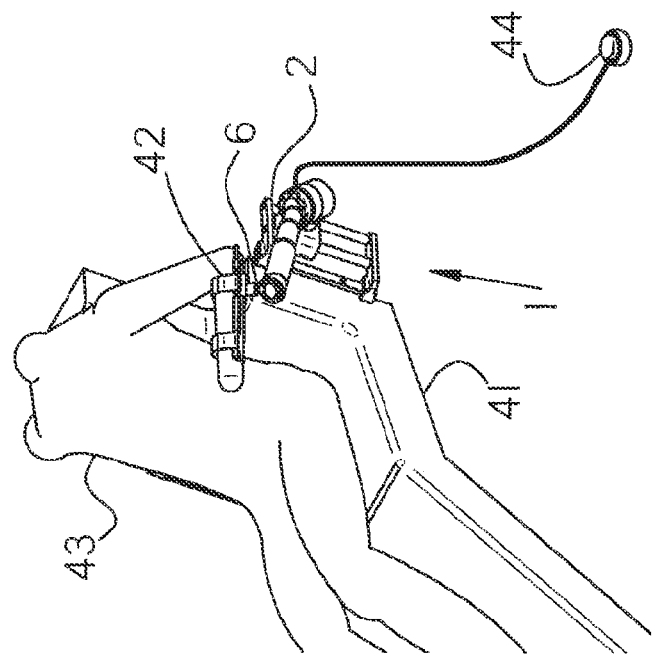
FIG. 2 is an example of use of the positioning apparatus of FIG. 1 as a limb support.

The foregoing and other objects, advantages and features of the present disclosure will become more apparent upon reading of the following nonrestrictive description of illustrative embodiments thereof, given by way of examples only with reference to the accompanying drawings.

Generally stated, the positioning apparatus described herein is concerned with a releasable lockable telescopic arm having two joint mechanisms at its ends. The joint mechanisms have each three rotational degrees of freedom. These joints and the telescopic arm may be locked and released using a locking mechanism described below. The locking mechanism is passively biased in a locked position and an external intervention is required for unlocking the locking mechanism in order to change the configuration of the positioning apparatus. The positioning apparatus offers a very wide range of adjustment over several degrees of freedom.

Lockable and releasable mechanisms are used for releasably locking the joint mechanisms in a desired position and the telescopic arm at a desired length. The joint mechanisms are passively locked using elastic energy, or potential energy, stored as pressure in a resilient member, for example a spring. Releasing the joint mechanisms is made using hydraulic pressure, pneumatic pressure, tension from a cable, push/pull rods, or a similar force that overcomes pressure from the resilient member.

Likewise, the telescopic arm may comprise a locking mechanism. The locking mechanism may be attached at an extremity of a first segment of the telescopic arm and is lockable on a second segment of the telescopic arm. The locking mechanism is locked using elastic energy stored as pressure in a resilient member, for example a spring. Releasing the locking mechanism is made using hydraulic pressure, pneumatic pressure, tension from a cable, push/pull rods, or a similar force that overcomes pressure from the resilient member.

In case of malfunction, for example when leakage causes a loss of hydraulic pressure, the positioning apparatus maintains its position at the joint mechanisms and at the arm locking mechanism because the elastic energy stored as pressure in the resilient member is not affected.

In one embodiment, a first intended use of the positioning apparatus is as a limb positioner for medical use. For example, the positioning apparatus may be used for surgery such as orthopaedic surgery, shoulder arthroscopic surgery, abdominal surgery, laparoscopic surgery, and/or the like. A second intended use of the positioning apparatus may be as a medical/surgical tool holder. These suggested uses are not limiting and are provided solely for illustration purposes.

In one embodiment, for a use as a reusable medical device, a limb interface for receiving a limb may be attached to a first joint mechanism of the positioning apparatus. The interface may then be in direct contact with a patient's limb. Alternatively, a tool interface for receiving a surgical or medical tool may be secured to the first joint mechanism. A second joint mechanism may be attached to a base interface or member which is securable to a base such as a surgical table for example.

Figure 1:
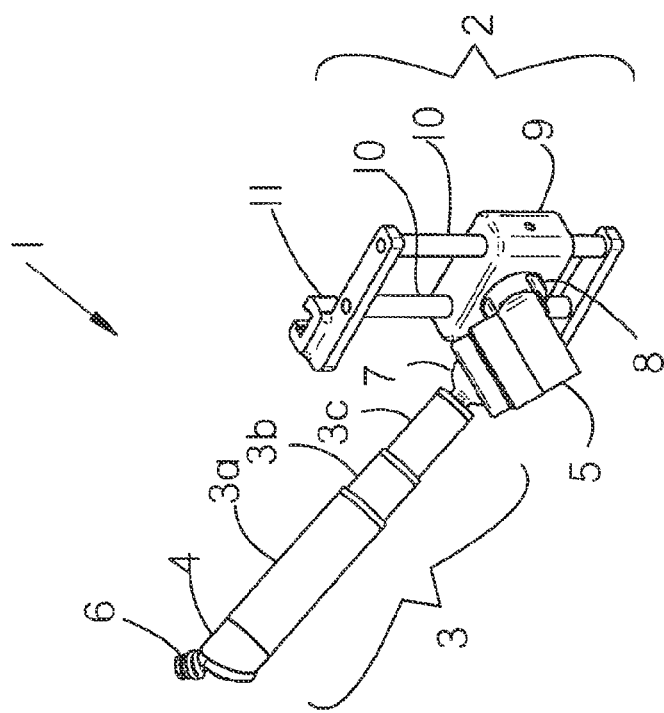
FIG. 1 is a perspective view of a positioning apparatus mounted on a base, in accordance with a first embodiment.

FIG. 1 illustrates one embodiment of a positioning apparatus 1 to be mounted to a base. The positioning apparatus 1 comprises a support or base member 2 which forms a securing device for attachment to the base such as a surgical table (not shown) for example. The positioning apparatus 1 comprises a telescopic arm 3 having three segments 3a, 3b and 3c, an upper spherical joint mechanism (not shown), a housing 4 covering the upper spherical joint mechanism, and a lower spherical joint mechanism 5. An accessory coupling 6 allows connection of the positioning apparatus 1 to various accessories, depending on its intended use. For example, the accessory coupling 6 may be used for securing a receiving member (not shown) adapted to receive an object such as a patient limb or a surgical tool. The spherical joint mechanisms each comprise a ball jointed to the telescopic arm, only the lower ball 7 is visible on FIG. 1. The lower spherical joint mechanism 5 is connected to an arm holder 9 of the support 2 via an arm 8. The support 2 further comprises height adjustment guides 10 and a table clamp 11. The positioning apparatus 1 is thus an arm-like mechanism used as a means to position, and to maintain in a desired position, a limb during a medical intervention, or a tool for various industrial applications. In an embodiment, the support 2 allows a position adjustment of the positioning apparatus 1, at its bottom-end, along a side of a surgical table. Various bases may be designed for various applications. The spherical joint mechanisms 4 and 5 allow a wide range of positions of an object attached to the accessory coupling 6.

The positioning apparatus 1 further comprises a locking device (not shown) operatively connected to the upper and lower joint mechanisms and the telescopic arm, and a lock activation device (not shown) for locking and releasing the locking device. When locked, the locking device lockingly interconnects the upper and lower joint mechanisms to the telescopic arm 3 so that no motion of the upper and lower joint mechanisms relative to the arm 3 is possible, and lockingly interconnects the arm segments 3a, 3b, and 3c together so that the length of the telescopic arm is fixed. Therefore, the positioning apparatus 1 is fixed in a given configuration. When the locking device is released, the telescopic arm 3 is free to move with respect to the upper and lower joint mechanisms and the arm segments 3a, 3b, and 3c are free to move the ones with respect to the others in order to adjust the positioning apparatus 1 from one configuration to another.

The locking device is passively biased in the locked position, i.e. in the absence of external intervention (when the lock activation device is not actuated) the configuration of the positioning apparatus is fixed and cannot be changed. In order to change the configuration of the positioning apparatus 1, the lock activation device must be activated.

In one embodiment, the locking device comprises a first locking unit operatively connected to the upper joint mechanism, a second locking unit operatively connected to the lower joint mechanism 5, a third locking unit secured to the arm segment 3b and operatively connected to the arm segment 3a, and a fourth locking unit secured to the arm segment 3c and operatively connected to the arm segment 3b. Each locking unit is passively biased in a locked position and may comprise a compressed elastic device and a piston operatively connected together. For the first and second locking units in the locked position and since the elastic device is in compression, the piston exerts a force on its respective joint mechanism which is prevented to move. For the third and fourth locking units in the locked position and since the elastic device is in compression, the piston exerts a force on the arm segment 3a and the arm segment 3b, respectively, in order to prevent any relative motion between the arm segments 3a, 3b, and 3c.

FIG. 2 is an example of use of the positioning apparatus of FIG. 1 as a limb support. The positioning apparatus 1, and the support 2 forming its base, are mounted on a surgical table 41. The table 41 is shown in a so-called "beach chair" position, but the positioning apparatus 1 could also be attached to most types of surgical chairs or beds, including dental chairs. A limb support 42, or limb interface, is connected to the positioning apparatus 1 via the accessory coupling 6. A patient 43 is shown to illustrate a possible use of the positioning apparatus 1 for orthopaedic surgery.

In one embodiment, the lock activation device comprises a pedal or foot pump 44 and fluidic connections filled with fluid such as oil for example. The fluidic connections fluidly connect the foot pump 44 to the locking units which each comprise an adjustable oil chamber of which one wall is formed by the piston. When a user depresses the foot pump, the force exerted by the user is transferred to the oil contained in the oil chambers. As a result, the oil contained in the oil chambers exerts a force on the pistons. For a given force exerted by the user on the foot pump 44, the force exerted by the oil contained in each oil chamber on its respective piston becomes greater than the force exerted by its respective elastic device on the respective piston. The locking units are then in the released position and the configuration of the positioning apparatus may be changed. When he has positioned the positioning apparatus 1 in a desired position, the user stops exerting the force on the foot pump 44 and the locking units return in the locked position, thereby maintaining the positioning apparatus 1 in the desired configuration.

Therefore, depressing the foot pump 44 with a foot may cause a release of the various locking mechanisms of the positioning apparatus 1, allowing for example a surgeon to effortlessly position a limb for surgery. Releasing the pedal removes all hydraulic pressure, whereafter resilient members within the various locking mechanisms maintain the positioning apparatus 1, and the patient's limb, in a desired position.

Those of ordinary skills in the art will readily appreciate that the positioning apparatus 1 may be used for various medical, veterinarian, or other applications. The positioning apparatus 1 may be attached to any base and to any accessory (not shown) attached to the accessory coupling 6. Non limiting examples of accessories may include tools, tool holders, computer displays, robots or robot components, and the like.

Figure 3:
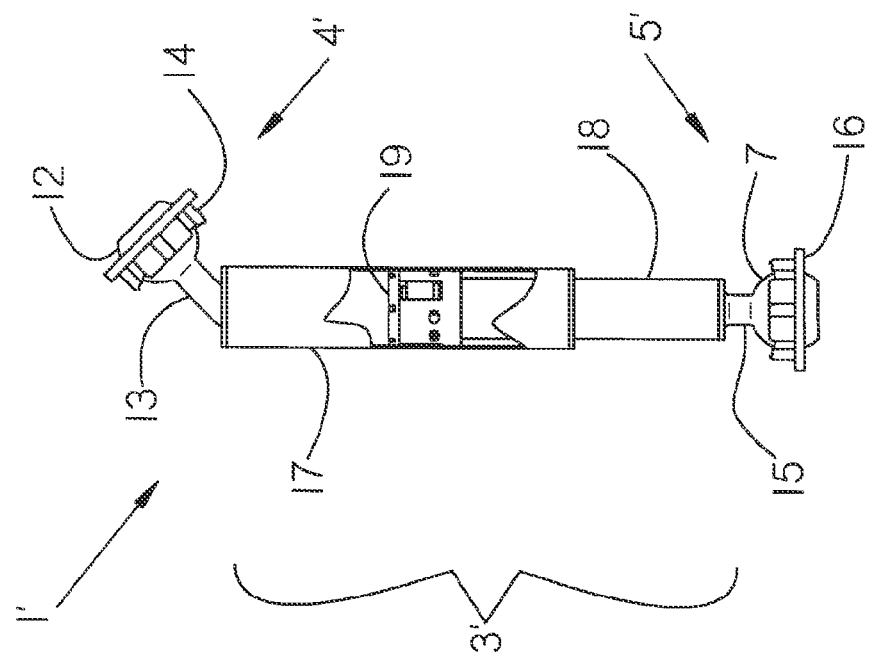
FIG. 3 is a side elevation, partial view of a positioning apparatus, in accordance with a second embodiment.

FIG. 3 illustrates another embodiment of a positioning apparatus 1'. Some parts of the upper and lower spherical joint mechanisms are omitted in FIG. 3 in order to show upper ball 12, the lower ball 7, connecting tubes 13 and 15, and covers 14 and 16. The balls 7 and 12 and their respective connecting tubes 13 and 15 are permanently joined, for example by adhesive or welding, and are fixedly attached to respective ends of the telescopic arm 3'. The covers 14 and 16 are put in place prior to bonding the lower ball 7 to the connecting tube 15 and to the segment 18 using adhesives, and prior to securing the upper ball 12 to the connecting tube 13 to the segment 17. The covers 14 and 16 as well as other parts of the spherical joint mechanisms 4' and 5' (shown on next Figures) may move around the balls 12 and 7, when in unlocked position. The telescopic arm 3' comprises an upper segment 17 and a lower segment 18. The upper segment 17 shows a telescopic arm locking mechanism 19, which will be described in details hereinbelow. While the present description refers to a telescopic arm 3' comprising two segments 17 and 18, it should be understood that the telescopic arm 3' may comprise more than two segments. Similarly, while the arm segment 18 fits and slides into the hollow arm member 17, other configurations are possible. For example, the arm segment 17 may comprise a rail on its outer surface in which the arm segment 18 may slide. It should also be understood that the shape, dimensions, and/or materials for the arm segments may vary and are chosen according to the needs of an intended application.

Of course, for use in some applications, the positioning apparatus 1' may be attached to a base located at an elevated point such as a ceiling for example, and an object supported by the positioning apparatus 1' may be located at a lower point. Those of ordinary skills in the art will appreciate that terms such as "upper", "lower", and the like are used for illustration purposes and are not meant to limit the present disclosure.

Figure 4:
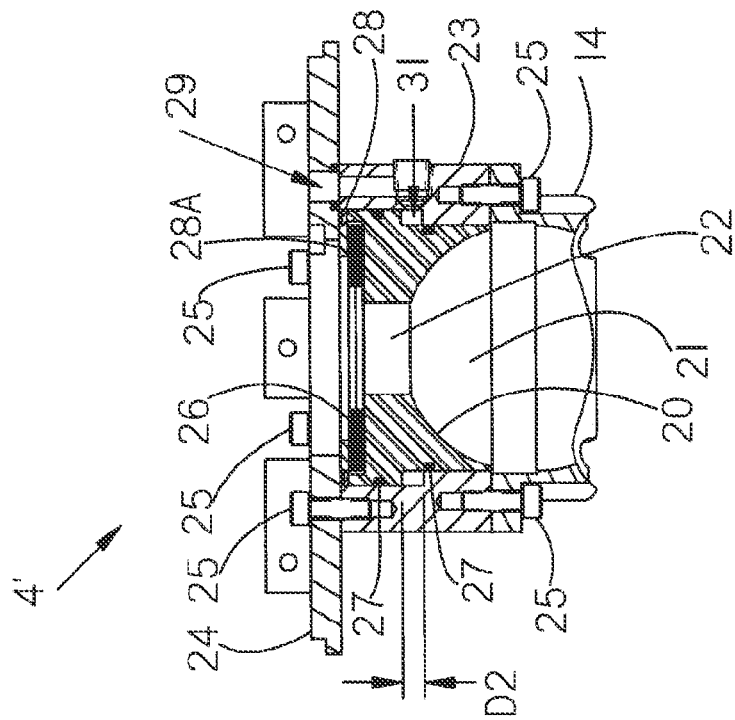
FIG. 4 is a side cutaway view of a movable spherical joint mechanism in unlocked position, in accordance with a first embodiment.

FIG. 4 is a side cutaway view of a movable spherical joint mechanism operatively connected to a locking device in an unlocked position, the locking device comprising a spring and a piston. FIG. 5 is a side cutaway view of the movable spherical joint mechanism and the locking device in a locked position. Considering at once FIGS. 4 and 5, the upper spherical joint mechanism 4' is shown in parts. It should be observed that its operating principles are the same as those of the lower spherical joint mechanism 5 and the following description of those principles applies to both spherical joint mechanisms. The upper spherical joint mechanism 4' comprises the cover 14, the ball 12 (omitted from FIGS. 4 and 5), a piston 20 having a hollow spherical portion 21 for positioning the ball 12 and a hollow cylindrical portion 22 for passage of hydraulic tubes (not shown) and like ancillary devices. The cover 14 is attached to a housing 23 that contains the piston 20, the housing 23 further attached to a coupling attachment 24 using various screws 25. The coupling attachment 24 is for attaching to an accessory coupling interface. The piston 20 abuts on springs 26, for example Belleville springs. Belleville springs are compact and minimize a length of the housing 23. Other types of springs, such as coil springs, or other types of resilient members, such as a compressible foam pad, may be used for some applications. Seals 27, such as o-rings gaskets for example, maintain a tight seal between the piston 20 and the housing 23. One or more shims 28A, or spacers, may be inserted between the coupling attachment 24 and the springs 26, being used as spacers in order to adjust a pressure applied by the springs 26 on the piston 20 and further on the ball 12. Additionally, one or more shims 28, or spacers, may be used to limit an upper movement of the piston 20. A screw (not shown) allows the piston 20 to move up and down, within the housing 23, while preventing its rotation within the housing 23. Most of the components of the upper spherical joint mechanism 4' are circular and a cutaway view will be similar in most angles. However the screws and an oil inlet 29 are located at discrete points around a diameter of the housing 23.

As shown on FIG. 5, the upper spherical joint mechanism 4' is in the locked position. The springs 26 push on the piston 20, which further pushes on the ball 12 (not shown), firmly keeping the ball 12 in position against the cover 14. The piston 20 and the cover 14 thus act as brake pads for the ball 12. A small gap 30 is created above the piston 20, between the piston 20 and the coupling attachment 24 or, if the shims 28 are present, between the shims 28 and the coupling attachment 24. A circular oil chamber 31 contains oil at a low pressure and has a minimized depth D1. As shown on FIG. 4, the upper spherical joint mechanism 4' is in the unlocked position. A higher oil pressure is induced via the oil inlet 29 within the oil chamber 31, inflating the oil chamber 31 until it reaches a maximized depth D2, pushing the piston 20 upward against the pressure of the springs 26. As the oil pressure creates a force to overcome pressure from the springs 26, the gap 30 disappears. At the same time, the piston 20 is no longer pushing on the ball 12, which is free to rotate, for example within a range of plus or minus 45 degrees around a central axis of the housing 23. It may be observed that zero, one or more shims 28A may be used to adjust the level of resistance for the upper spherical joint mechanism 4' in order to set the predefined oil pressure at which the upper spherical joint mechanism will unlock.

In an embodiment, pneumatic pressure could be used instead of hydraulic pressure within the upper spherical joint mechanism 4. Those of ordinary skills in the art will appreciate that the upper spherical joint mechanism's operating principles will not be essentially modified. They will be able to adapt tolerances and sealing means within the joint to use pneumatic pressure. In another embodiment, a cable, for example a Bowden cable comprising an inner flexible wire within an outer hollow cable housing, similar to cables used for ordinary bicycle brakes, may be used to pull on the piston 20, pulling force being applied from the top of the piston 20 so to overcome pressure from the springs 26.

FIG. 6 is a side cutaway view of a movable spherical joint mechanism attached to a telescopic arm and to a base. The lower spherical joint mechanism 5 differs from the upper spherical joint mechanism 4 in some details, but not in its operating principles. The lower spherical joint mechanism 5 comprises the ball 7, which is attached to the lower segment 18 via the connecting tube 15. Also shown are the cover 16, a housing 32, a base attachment 33 comprising the arm 8 connected to the arm holder 9 of the support 2, various screws 25, a piston 34, springs 35 maintained in place by spring holders 45, and an oil chamber 36. Oil enters the oil chamber 36 via an oil inlet 37 connected to a hydraulic fitting 38, which is itself connected to a hydraulic pump (not shown). It may be observed that the upper spherical joint mechanism 4' of FIGS. 4 and 5 comprises an oil inlet 29 connected to a hydraulic fitting (not shown) similar to the oil inlet 37 and to the hydraulic fitting 38 of FIG. 6. A bleeding plug 39 and a base plug 39A allow maintenance of the lower spherical joint mechanism 5. An oil tube 40, cables (not shown) or similar ancillary devices may pass through passages of the springs 35, a ball 7, a connecting tube 15, and a lower segment 18. Oil pressure entering via the hydraulic fitting 38 may be applied to release the lower spherical joint mechanism 5, allowing a wide range of adjustment of a position of the telescopic arm 3. When the oil pressure is removed, pressure applied by the springs 35 on the piston 34 and further on the ball 7 maintains the ball 7 against the cover 16, locking the position of the telescopic arm 3.

A length of the telescopic arm 3 is defined by a desired position of an object attached to the accessory coupling 6. The telescopic arm 3' comprises two (2) segments 17 and 18, one sliding within the other one, so that the telescopic arm 3 may be elongated or retracted to the desired length. The desired position is maintained by friction between the segments 17 and the arm locking mechanism 19 attached to the segment 18. In an embodiment, the telescopic arm 3' may comprise more segments and a plurality of arm locking mechanisms.

Figure 7:
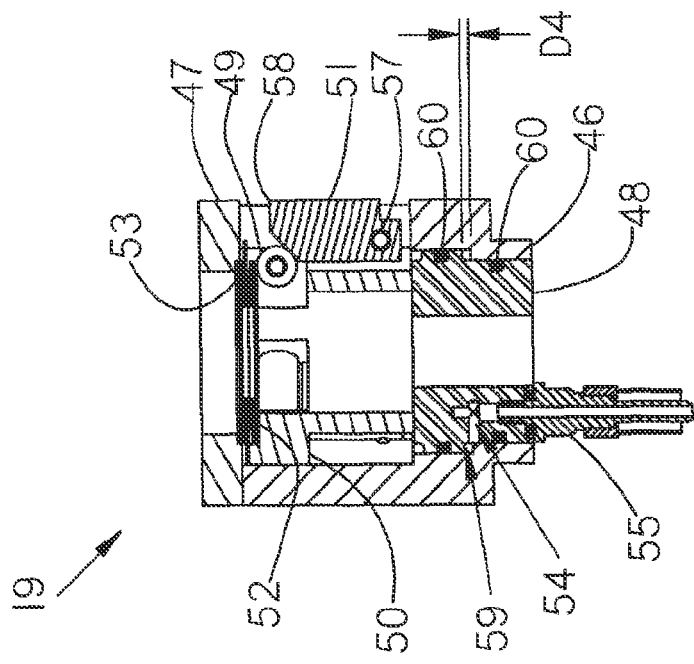
FIG. 7 is a side cutaway view of a telescopic arm locking mechanism in locked position, in accordance with a first embodiment.
Figure 8:
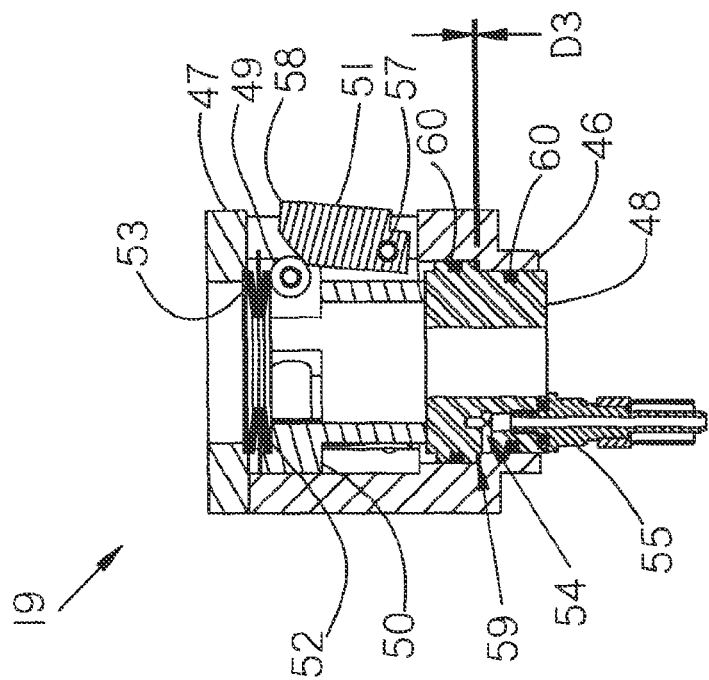
FIG. 8 is a side cutaway view of the telescopic arm locking mechanism of FIG. 7 in unlocked position.

Energy stored in a resilient member mechanism forces the telescopic arm 3 to maintain a fixed length until an opposite force overcomes pressure from the resilient member mechanism. FIG. 7 is a side cutaway view of a telescopic arm locking mechanism in locked position. FIG. 8 is a side cutaway view of a telescopic arm locking mechanism in unlocked position. The arm locking mechanism 19 comprises a housing 46, a cap 47, a piston 48 that maintains a tight seal against the housing 46 by use of o-rings 60, one or more rollers 49 positioned on a circumference of a support 50, brake pads 51, which may be metallic pads, a resilient member such as springs 52, which in an embodiment may be Belleville springs, shims 53, an oil inlet 54 and a hydraulic fitting 55.

The arm locking mechanism 19 may be attached at the top of the segment 18, which as shown on FIG. 3, has a smaller diameter compared to the segment 17. Attachment of the arm locking mechanism 19 to the segment 18 may be by bonding, welding, gluing, tight insertion, or any suitable means. The segment 18 and the arm locking mechanism 19 are thus inserted within the segment 17. As shown on FIG. 7, the arm locking mechanism 19 is in locked position. Pressure from the springs 52 push on the support 50, creating a gap 61 between the support 50 and the cap 47. As the support 50 is pushed down, the rollers 49 push on the brake pads 51, which rotate about respective axis 57, a tip 58 of each brake pad 51 moving outwardly and applying pressure on an inner surface of the segment 17. Pressure from the brake pads 51 on the inner surface of the segment 17 maintains a relative position between the two segments 17 and 18, thereby maintaining a length of the telescopic arm 3'. The support 50 also applies pressure on the piston 48. An oil chamber 59 has a minimized depth D3 and has a low hydraulic pressure.

In one embodiment, the arm locking mechanism 19 may be mounted within the segment 17 in various positions. When the segment 17, which has a wider diameter, is located above the narrower segment 18 and when the arm locking mechanism 19 is mounted vertically as shown on FIG. 7—the cap 47 being in a higher position above the piston 48—weight on the telescopic arm 3' may tend to push down the segment 17. Because of the configuration of the brake pad 51, which applies pressure on the inner surface of the segment 17 at its tip 58, this weight applies an added friction force of the brake pad 51 on the segment 17.

FIG. 8 shows that the oil chamber 59 has extended to a maximized depth D4 when high hydraulic pressure from the hydraulic fitting 55 enters the oil chamber 9 through the oil inlet 54. This oil pressure creates a force that pushes the piston 48 against the support 50, the support 50 pushing against the springs 52, overcoming their pressure. The gap 61 disappears. As the support 50 moves up, the rollers 49 no longer push the brake pads 51, which may move inwardly and which no longer apply pressure on the inner surface of the segment 17. This removes any restriction to the length of the telescopic arm 3', which may then be extended or shortened as desired. In an embodiment, application of the oil pressure may be controlled by the pedal 44.

Figure 9:
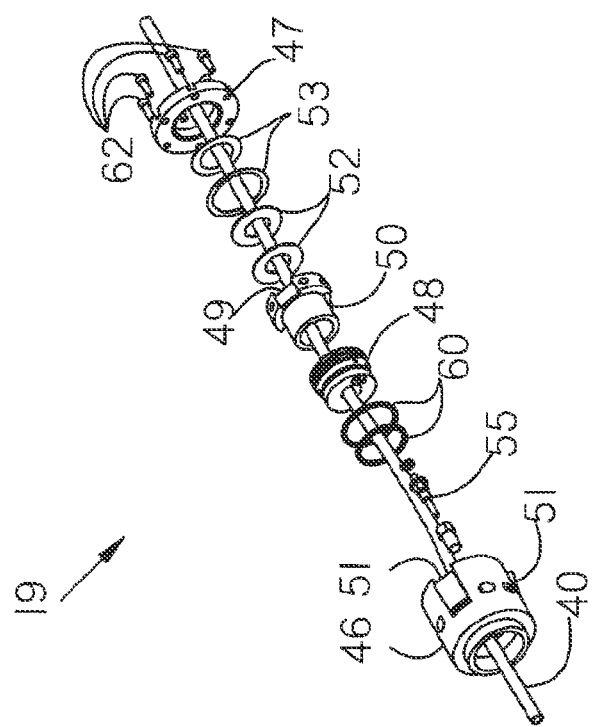
FIG. 9 is an exploded view of a telescopic arm locking mechanism, in accordance with an embodiment.

FIG. 9 is an exploded view of a telescopic arm locking mechanism. It may be observed that the arm locking mechanism 19 comprises generally circular members having inner passages for the oil tubes 40, cables (not shown) and like devices. Various parts of the arm locking mechanism 19 are held together using screws 62.

Figure 10:
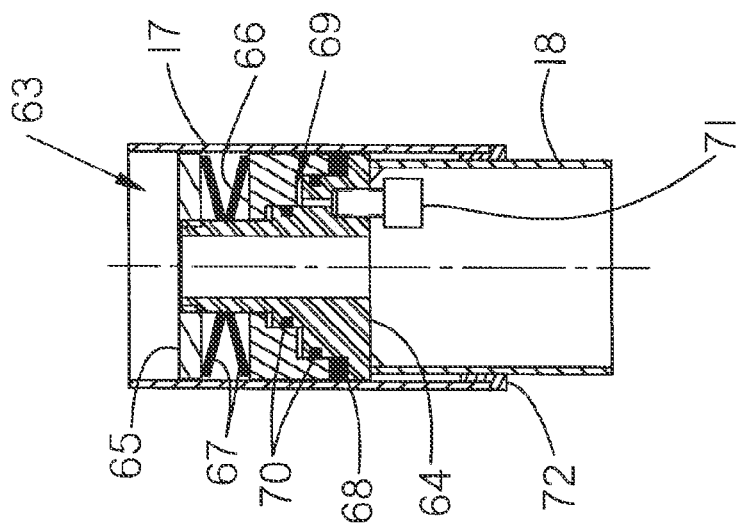
FIG. 10 is a side cutaway view of a telescopic arm locking mechanism, in accordance with a second embodiment.

FIG. 10 is a side cutaway view of another example of telescopic arm locking mechanism. An arm locking mechanism 63 is attached, for example by gluing or welding, at the top of the segment 18 and is located, with the top of the segment 18, within the segment 17. The arm locking mechanism 63 comprises a generally frusto-pyramidal base 64, a cap 65 screwed onto the base 64, a piston 66 abutting on springs 67 which further abut on the cap 65, and one or more deformable polymeric brake pads 68. One brake pad 68 may fill a full circumference of the arm locking mechanism 63 or, alternatively, several brake pads 68 may be positioned around the circumference. When in a resting position, the springs 67 push down on the piston 66, thereby elastically deforming the brake pads 68 which in turn push against an internal surface of the segment 17. In order to release the arm locking mechanism 63, hydraulic pressure may be applied in an oil chamber 69, confined by o-rings 70, via a hydraulic inlet 71. The hydraulic pressure creates a force that pushes the piston 66 upward against the springs 67, overcoming their downward pressure. As the piston 66 moves upwards, the one or more brake pads 68 regain a somewhat circular sectional shape, thereby no longer pushing against the internal surface of the segment 17. Relative movement of the segments 17 and 18 is then possible. A stop 72 may prevent the arm locking mechanism 63 and the segment 18 from becoming disengaged from the segment 17.

Variations of the arm locking mechanisms 19 or 63 will come to mind to those of ordinary skill in the art. For example, in an embodiment, coil springs or a compressible foam pad may substitute for the Belleville springs. The type of resilient member and the presence and number of shims may vary according to expected weight applied on the telescopic arm 3', materials used, and the like. In an embodiment, pneumatic pressure could be used instead of hydraulic pressure within the arm locking mechanisms 19 or 63. In another embodiment, a Bowden cable may be used to pull on the pistons 48 or 66. In another embodiment, an equivalent arm locking mechanism, fixedly attached to the segment 17, may comprise a bore for insertion of the segment 18. This arm locking mechanism may thus have brake pads that push inwardly on an outer surface of the segment 18, when in locked position.

Considering any one of FIGS. 4-6, and 7-10, each one of the spherical joint mechanisms and each one the arm locking mechanisms comprises a support (23, 32, 46, 64), a movable member (12, 7, 51) or a deformable member (68), a piston (20, 34, 48, 66) capable of moving along an axis of the support, a resilient member (26, 35, 52, 67) applying pressure on the piston for transmitting the pressure to the movable or deformable member in order to lock the movable or deformable member, and oil enclosed in a chamber (31, 36, 59, 69) for exerting on the piston a force opposing the pressure from the resilient member, the oil pressure being controlled by a pump. Applying the force on the piston overcomes the pressure from the resilient member and releases the movable or deformable member.

FIG. 11 is another example of use of a positioning apparatus as a limb support, 30 showing another base. The positioning apparatus 1 is mounted on a base 73 attached to the surgical table 41.

FIGS. 12A and 12B illustrate a further embodiment of a positioning apparatus 100. The positioning apparatus 100 comprises a telescopic member or arm 102 having a first or upper end 102a and a second or lower end 102b. A first or upper joint mechanism 104 and a second or lower joint mechanism 106 are secured at the ends 102a and 102b of the telescopic arm 102, respectively. The positioning apparatus 100 further comprises an interface member 108 secured to the upper joint mechanism 104 for receiving an object thereon, and a base member 110 for removably securing the positioning apparatus 100 to a base.

While in the illustrated embodiment the interface member 108 is adapted to receive an arm, it should be understood that any adequate interface member for receiving an object may be used. For example, the interface member may be adapted to receive a limb other than an arm such as a leg for example. In another example, the interface member may be adapted to receive a surgical or medical tool.

While in the illustrated embodiment the base member 110 comprises an elongated member 112 having one end secured to the lower joint mechanism 106 and an adjustable clamp 114 secured at the other end of the elongated member 112 for removably securing the positioning apparatus 100 to a surgical table for example, it should be understood that other configurations for the base member 110 may be used. For example, the base member 110 can be adapted for being removably or permanently secured to any adequate base such as a floor, a wall, a ceiling, a bed, a chair, or the like. The base member 110 may only comprise a plate fixedly secured to the lower joint mechanism 106. The plate may be removably secured to a base via fasteners for example. Alternatively, the plate may be fixedly secured to the base via adhesive or welding for example.

Figure 13:
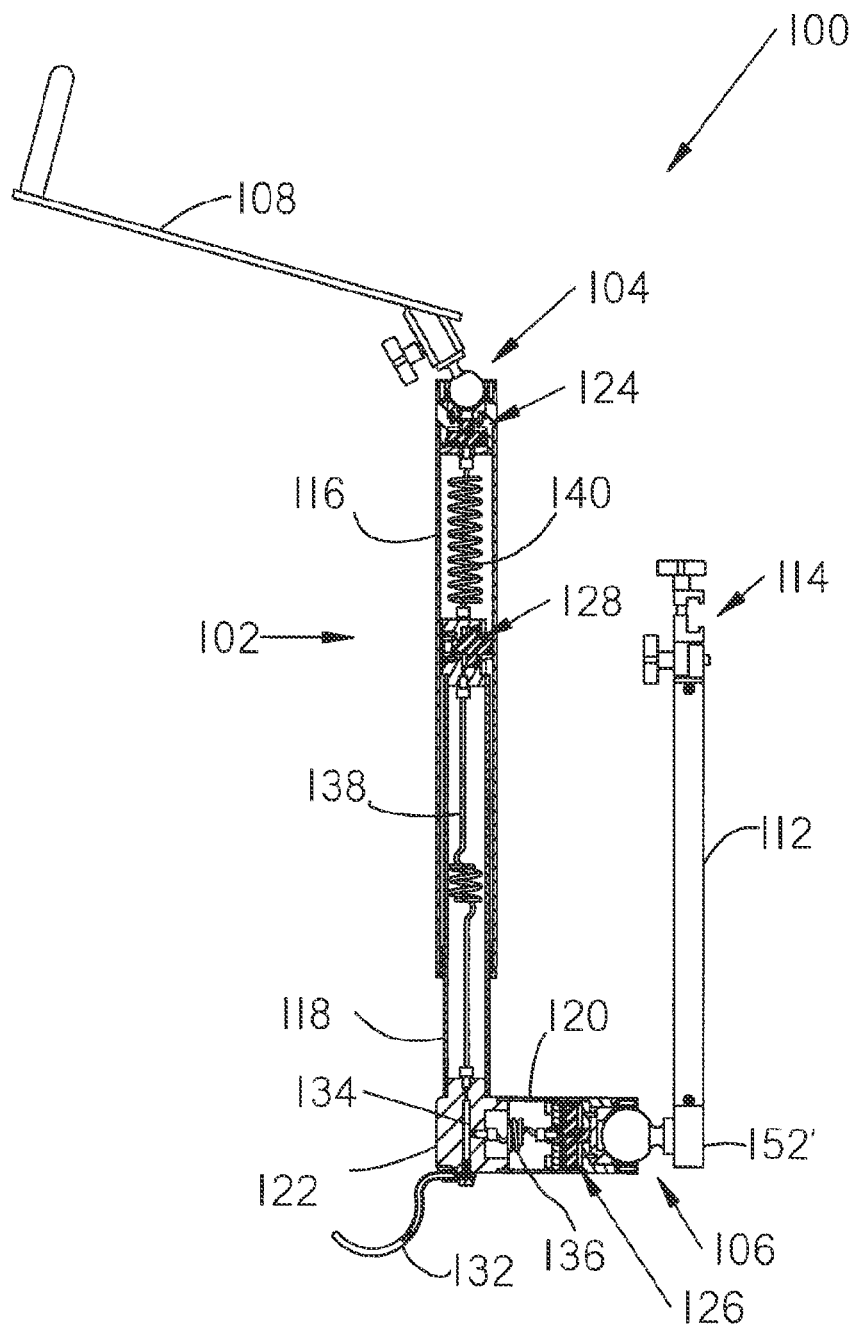
FIG. 13 is a cross-sectional side view of the positioning apparatus of FIG. 12A.

As illustrated in FIG. 13, the telescopic arm 102 comprises two hollow elongated members 116 and 118 which are adapted so that the hollow member fits and slides into the hollow member 116. The telescopic arm 100 comprises a third hollow elongated member 120 connected at one end of the hollow member 118 via a connector 122, thereby providing the telescopic arm 102 with a substantially L-shape. The hollow member 120 is further connected to the lower joint mechanism 106.

Three locking devices 124, 126, and 128 are operatively connected to the upper joint mechanism 104, the lower joint mechanism 106, and the hollow member 118, respectively. The locking devices 124 and 126 are used for selectively locking the joint mechanisms 104 and 106, respectively, in a desired position while the locking device 128 is used for fixing the length of the telescopic member 102 at a desired length. As described below, the locking devices 124, 126, and 128 are passively locked in a locked position, thereby preventing any position adjustment of the joint mechanisms 104 and 106 and any length adjustment for the telescopic member 102 without external intervention.

The external intervention is provided via a lock activation device 130, as illustrated in FIG. 12A. In the illustrated embodiment, the lock activation device 130 is a pump fluidly connected to the locking devices 124, 126, and 128. A fluidic connection 132 fluidly connects the pump 130 to a T-shaped fluidic manifold 134. The fluidic connector 134 is inserted into the connector 122 and comprises an inlet fluidly connected to the fluidic connection 132 and two outlets. The first outlet is fluidly connected to the locking unit 126 via a fluidic connection 136 extending through the hollow member 120, and the second outlet is fluidly connected to the locking unit 128 via a fluidic connection 138 extending inside the hollow arm member 118. The locking unit 128 is further connected to the locking unit 124 via a fluidic connection 140 extending inside the hollow arm member 116. The fluidic connections 132-140, the pump 130, and the chambers described below are filled with oil, and form a substantially hermetical closed-circuit from which oil cannot substantially leak.

FIGS. 14A and 14B illustrate the upper joint mechanism 104 in a locked position and a released or unlocked position, respectively. The joint mechanism 104 comprises a ball 150, a connecting tube 154 for connection to an interface connector 152 of the interface member 108, and a casing 156. The connecting tube 154 interconnects the ball 150 and the interface connector 152 which is used for connecting the interface member 108 to the upper joint mechanism 104.

The casing 156 comprises a first recess portion 158 for receiving the ball 150 and a cover 160 comprising a central aperture partially encloses the ball 150 within the recess portion 158. The casing 156 further comprises a second recess portion 162 for receiving the locking device 124 and a cover 164 for enclosing the locking device 124 within the recess portion 162.

The locking unit 124 comprises two Belleville springs 170 and a piston assembly formed of a piston 172, a set screw 174, and a brake pad 176. The set screw is used for adjusting the resistance of the Belleville springs, and therefore the force required for unlocking the locking unit 124. The brake pad 176 has a substantially cylindrical shape and its internal shape substantially matches that of the ball 150 so that the ball seats into the brake pad 176. The set screw 174 connects the piston 172 to the brake pad 176. Guides 178 are used to guide the translation of the brake pad 176 and prevent the brake pad 176 from rotating. The Belleville springs 170, while in compression, are enclosed between the cover 164 and the piston 172. The piston assembly is used for transferring the pressure force exerted by the Belleville springs 170 to the ball 150. A space between the piston 172 and the casing 156 defines an oil chamber 180 for receiving oil therein. The oil chamber 180 is fluidly connected to the fluidic connection 140 via a manifold 182 extending through the piston member 172 and the cover 164. Seals 181 are used for preventing the oil contained in the oil chamber 180 from leaking out thereof.

The locking unit 124 is passively biased in the locked position illustrated in FIG. 14A. In the locked position, the force exerted by the oil present in the oil chamber 180, if any, on the piston 172 is less than the force exerted by the springs 170 on the piston 172. Therefore, the resulting force is transferred to the ball 150 via the piston assembly and the ball 150 abuts against the cover 160, thereby being prevented from moving via friction and/or deformation forces. The joint mechanism 104 is then locked. Since no external intervention is required for maintaining the locking device 124 in the locked position and locking the joint mechanism 104, the locking device 124 is passively biased in the locked position.

Upon activation of the pump 130, the pressure of the oil within the oil chamber 180 increases. When the force exerted by the oil contained in the oil chamber 180 on the piston 172 becomes greater than the force exerted by the springs 170 on the piston 172, the height of the oil chamber increases and the springs 170 is further compressed. The brake pad 176 is then disengaged from the ball 150 which is free to move in the recess 158, as illustrated in FIG. 14B.

Figures 15A, 15B:
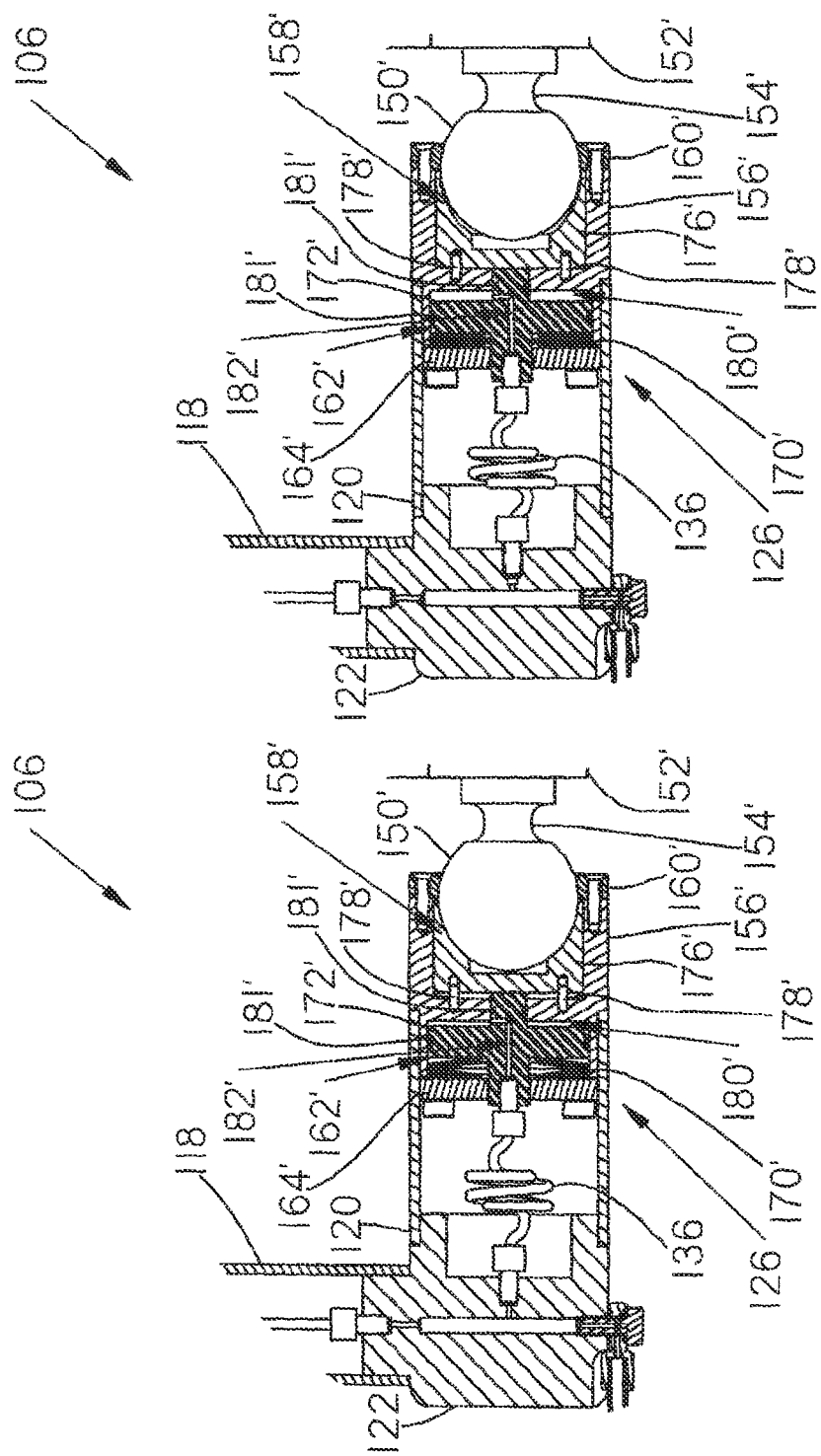
FIGS. 15A and 15B illustrate a cross-sectional view of a lower joint mechanism of the positioning apparatus of FIG. 12A, in a locked and released position, 20 respectively.

FIGS. 15A and 15B illustrate the lower joint mechanism 106 in a locked position and a released or unlocked position, respectively. The joint mechanism 106 comprises a ball 150', a base member connector 152', a connecting tube 154', and a casing 156'. The connecting tube 154' interconnects the ball 150' and the base member connector 152' which is used for connecting the base member 112 to the lower joint mechanism 106. The casing 156' comprises a first recess portion 158' for receiving the ball 150' and a cover 160' comprising a central aperture partially encloses the ball 150' within the recess portion 158'. The casing 156' further comprises a second recess portion 162' for receiving the locking device 126 and a cover 164' for enclosing the locking device 126 within the recess portion 162'.

The locking unit 126 comprises two Belleville springs 170' and a piston assembly formed of a piston 172' and a brake pad 176'. The brake pad 176' has a substantially cylindrical shape and its internal shape substantially matches that of the ball 150' so that the ball partially seats into the brake pad 176'. The piston members 172' and 176' are connected together. Guides 178' are used to guide the translation of the brake pad 176' and prevent the brake pad 176' from rotating. The Belleville springs 170', while in compression, are enclosed between the cover 164' and the piston 172'. The piston assembly is used for transferring the pressure force exerted by the Belleville spring 170' to the ball 150'. A space between the piston 172' and the casing 156' defines an oil chamber 180' for receiving oil therein. The oil chamber 180' is fluidly connected to the fluidic connection 136 via an aperture 182' extending through the piston member 172' and the cover 164'. Seals 181' are used for preventing the oil contained in the oil chamber 180' from leaking out thereof.

The locking unit 126 is passively biased in the locked position illustrated in FIG. 15A. In the locked position, the force exerted by the oil present in the oil chamber 180', if any, on the piston 172' is less than the force exerted by the springs 170' on the piston 172'. Therefore, the resulting force is transferred to the ball 150' via the piston assembly and the ball 150' abuts against the cover 160', thereby being prevented from moving via friction and/or deformation forces. The joint mechanism 106 is then locked. Since no external intervention is required for maintaining the locking device 126 in the locked position and locking the joint mechanism 106, the locking device 126 is passively biased in the locked position.

Upon activation of the pump 130, the pressure of the oil within the oil chamber 180' increases. When the force exerted by the oil contained in the oil chamber 180' on the piston 172' becomes greater than the force exerted by the springs 170' on the piston 172', the height of the oil chamber 180' increases and the springs 170' are further compressed. The brake pad 176' is then disengaged from the ball 150' which is free to move in the recess 158', as illustrated in FIG. 15B. The locking unit 126 is then in the unlocked or released position.

Figure 16B:
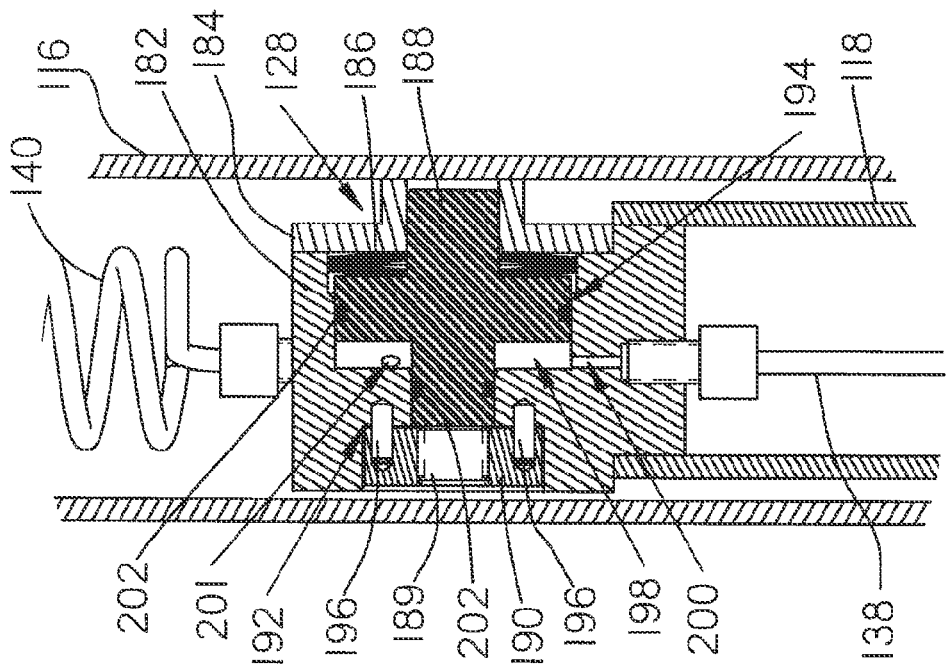
FIGS. 16A and 16B illustrate a cross-sectional view of a locking device for releasably locking an arm of the positioning apparatus of FIG. 12A, in a locked and released position, respectively.
Figure 16A:
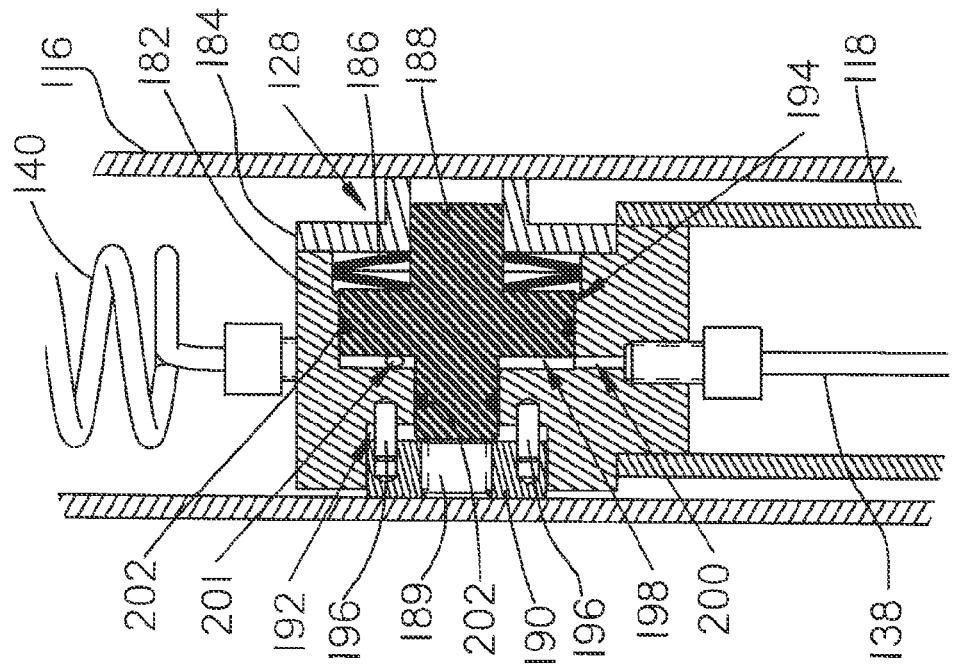

FIGS. 16A and 16B illustrate the locking unit 128 in a locked position and an unlocked or released position, respectively. The locking unit 128 is secured at one end of the arm member 118 and is located within the arm member 116. The locking unit 128 comprises a casing 182, a cover 184, two Belleville springs 186, and a piston assembly comprising a piston 188, a set screw 189, and a brake pad 190. The casing 182 comprises a first recess portion 192 for receiving the brake pad 190 and a second recess portion 194 for receiving the piston 188 and the springs 186. The cover 184 is used for enclosing the piston member 188 and the springs 186 in the second recess portion 194. The springs 186, while in compression, are sandwiched between the cover 184 and the piston member 188. An aperture is present through the casing 182 for connecting the first and second recess portions 192 and 194. A portion of the piston 188 extends through the aperture to connect with the brake pad 190 via the set screw 189. The set screw is further used for adjusting the compression of the springs 186, and therefore setting the force at which the locking unit 128 will unlock. Guides 196 are used to guide the translation of the brake pad 190 and prevent the brake pad 190 from rotating.

The piston assembly is used for transferring the pressure force exerted by the Belleville springs 186 to the brake pad 190. A space between the piston member 194 and the casing 182 defines an oil chamber 198 for receiving oil therein. The oil chamber 198 is fluidly connected to the fluidic connection 138 via a first aperture 200 extending through the casing 182. The oil chamber 198 is further fluidly connected to the fluidic connection 140 via a second aperture 201 extending through the casing 182. Seals 202 are used for preventing the oil contained in the oil chamber 198 from leaking out thereof.

The locking unit 128 is passively biased in the locked position illustrated in FIG. 16A. In the locked position, the force exerted by the oil present in the oil chamber 198, if any, on the piston 188 is less than the force exerted by the springs 186 on the piston 188. Therefore, the resulting force is transferred to the brake pad 190 via the piston 188 which firmly abuts against the arm member 116. The cover 184 also firmly abuts against the internal surface of the arm member 116, thereby preventing any relative motion between the two arm members 116 and 118 via friction and/or deformation forces. The telescopic arm 102 is then locked, and its length is fixed. Since no external intervention is required for maintaining the locking device 128 in the locked position and locking the telescopic arm 102, the locking device 128 is passively biased in the locked position.

Upon activation of the pump 130, the pressure of the oil within the oil chamber 198 increases. When the force exerted by the oil contained in the oil chamber 198 on the piston member 188 becomes greater than the force exerted by the springs 186 on the piston 188, the width of the oil chamber 198 increases and the springs 186 is further compressed. The brake pad 190 is then disengaged from the internal surface of the arm member 116, as illustrated in FIG. 16B. The arm member 118 may slide within the arm member 116, and the length of the telescopic arm 102 may be adjusted to a desired length. The locking unit 128 is then in the unlocked or released position.

In one embodiment, a single activation of the pump 130 allows for the concurrent releasing of the three locking units 124, 126, and 128, and therefore the adjustment of the configuration of the joint mechanisms 104 and 106 and the length of the telescopic arm 102. Since the oil chambers 180, 180', and 198 are fluidly connected together, the activation of the pump 130 causes a pressure increase for the oil contained in the oil chambers 180, 180', and 198. In one embodiment, the springs 170, 170', and 186 and their respective compression are chosen so that the locking units 124, 126, and 128 are substantially concurrently released when the oil pressure reaches a given pressure. In another embodiment, the locking units may be released sequentially. For example, the springs 170, 170', and 186 and their respective compression are chosen so that the locking unit 124 is first released when the oil pressure reaches a first given pressure, and the locking units 126 and 128 are substantially concurrently released when the oil pressure reaches a second and greater pressure.

It should be understood that the length of the fluidic connections 136, 138, and 140 is chosen so as to allow the piston assemblies for the locking units 124, 126, and 128 to move and the arm member 118 to slide within the arm member 116.

In one embodiment, the pump 130 is a foot pump to be manually activated by a user. In another embodiment, the pump is electrically or pneumatically driven.

While the present description refers to a hydraulic/pneumatic lock activation device using a fluid such as oil, water, air, and the like for unlocking the locking units, it should be understood that any adequate lock activation device which allows for further compression the elastic/resilient member of the locking device in order to unlock the joint mechanism may be used. For example, a cable may be secured to the elastic/resilient member of the locking device and the further compression of the elastic/resilient member can result from a tension exerted on the cable. In another example, push/pull/torsion rods may be used for further compressing the elastic/resilient member in order to overcome pressure from the resilient member.

Figure 17:
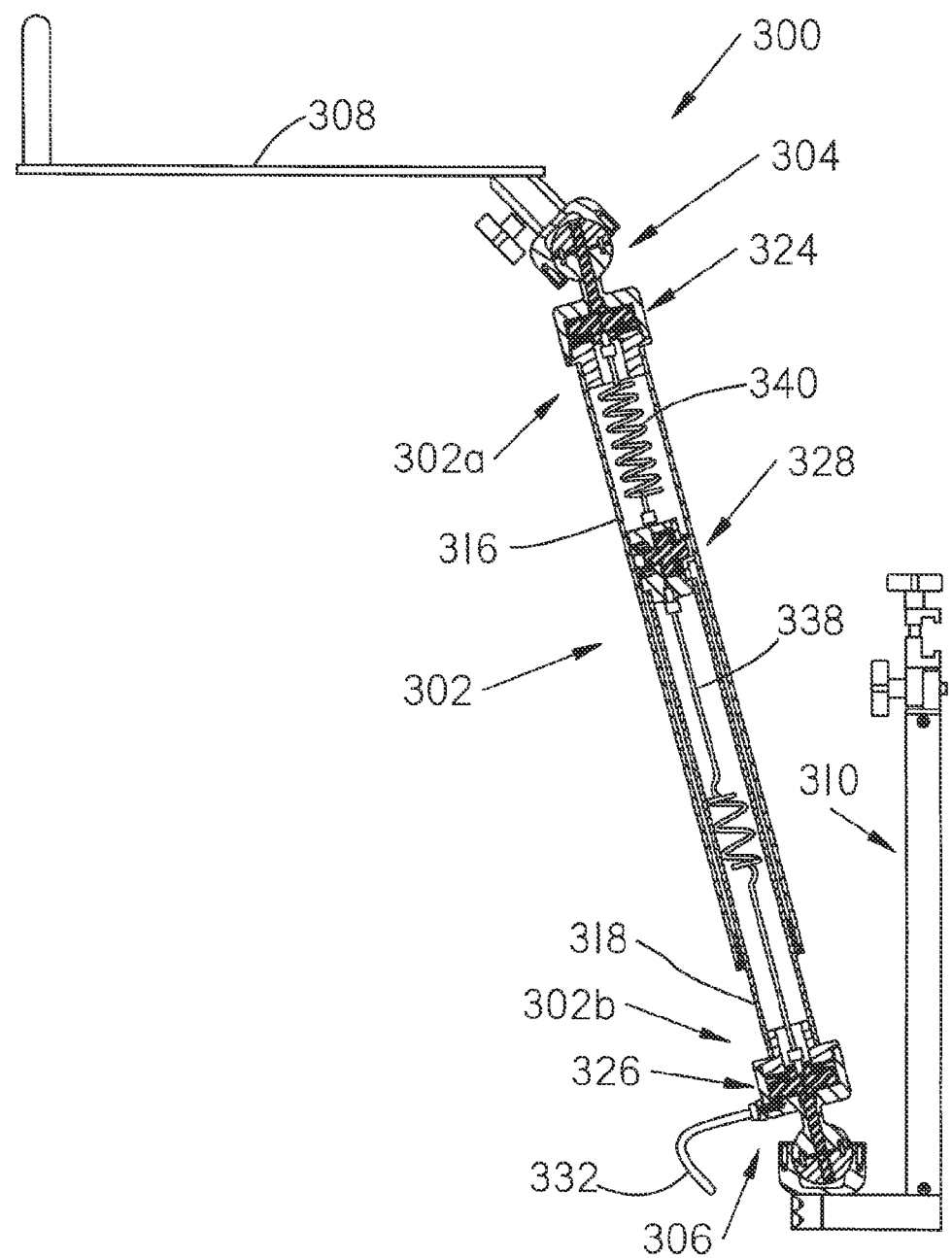
FIG. 17 is a cross-sectional side view of a positioning apparatus, in accordance with a further embodiment.

FIG. 17 illustrates a further embodiment of a positioning apparatus 300. The positioning apparatus 300 comprises a telescopic member or arm 302 having a first or upper end 302a and a second or lower end 302b. A first or upper joint mechanism 304 and a second or lower joint mechanism 306 are secured at the ends 302a and 302b of the telescopic arm 302, respectively. The positioning apparatus 300 further comprises an interface member 308 secured to the upper joint mechanism 304 for receiving an object thereon, and a base member 310 for removably securing the positioning apparatus 300 to a base.

The telescopic arm 302 comprises two hollow elongated members 316 and 318 which are adapted so that the hollow member 318 fits and slides into the hollow member 316. The telescopic arm 300 is further connected to the L-shaped base member 310 via the joint mechanism 306.

Three locking devices 324, 326, and 328 are operatively connected to the upper joint mechanism 304, the lower joint mechanism 306, and the hollow member 316, respectively. The locking devices 324 and 326 are used for selectively locking the joint mechanisms 304 and 306, respectively, in a desired configuration while the locking device 328 is used for fixing the length of the telescopic member 302 at a desired length. As described below, the locking devices 324, 326, and 328 are passively biased in a locked position, thereby preventing any position adjustment of the joint mechanisms 304 and 306 and any length adjustment for the telescopic member 302 without external intervention.

The external intervention is provided via a lock activation device (not shown), such as a pump fluidly connected to the locking devices 324, 326, and 328. A fluidic connection 332 fluidly connects the pump 130 to the locking unit 326. A second fluidic connection 338 extending within the arm member 318 fluidly connects the locking unit 326 to the locking unit 328, and a third fluidic connection 340 extending within the arm member 316 fluidly connects the locking unit 328 to the locking unit 324.

The fluidic connections 332, 338, and 340, the pump, and the chambers described below are filled with oil, and form a substantially hermetical closed-circuit from which oil cannot substantially leak.

FIGS. 18A and 18B illustrate the lower joint mechanism 306 in a locked position and a released or unlocked position, respectively. The joint mechanism 306 comprises a ball 350, a socket 352, a connecting tube 354, and a casing 356. The ball 350 comprises a first hemispherical portion 350a fixedly secured to the casing 356 via the connecting tube 354, and a second hemispherical portion 350b movable with respect to the first hemispherical portion 350a. Guides 351 are used for guiding the translation of the second hemispherical portion 350b with respect to the first hemispherical portion 350a, and preventing any rotational motion of the second hemispherical portion 350b with respect to the first hemispherical portion 350a. The socket 352 comprises a socket casing 352a and a socket cover 352b. The socket casing 352a is provided with a recess portion 358 for receiving at least a part of the ball 350. The socket cover 352b is provided with an aperture 360 through which a part of the ball 350 extends. The socket cover 352b is used for enclosing the ball 350 within the socket 352, while allowing motion of the ball 350 within the socket 352.

The casing 356 comprises a casing recess portion 362 for receiving the locking device 326 and a cover 364 for enclosing the locking device 326 within the recess portion 362.

The locking unit 326 comprises two Belleville springs 370 and a piston 372. The piston 372 is operatively connected to the Belleville springs 370 at one end, and to the second hemispherical portion 350b at the other end. The piston receiving aperture extends through the casing 356, the connecting tube 354, and the first hemispherical portion 350a. The piston 372 extends through the piston receiving aperture to connect the Belleville spring 370 to the second hemispherical portion 350b. The piston 372 is used for transferring the compression force exerted by the Belleville springs 370 to the second hemispherical portion 350b. For example, the piston 372 may abut against the second hemispherical portion 350b for transferring the Belleville spring force thereto. In another embodiment, the piston 372 is fixedly secured to the second hemispherical portion 350b.

The Belleville springs 370, while in compression, are enclosed between the cover 364 and the piston member 372. The cover is further secured to the arm member 318 in order to secure the joint mechanism 306 thereto. A space between the piston 372 and the casing 356 defines an oil chamber 380 for receiving oil therein. The oil chamber 380 is fluidly connected to the fluidic connection 332 via an aperture 382 extending through the casing 356. Seals 381 are used for preventing the oil contained in the oil chamber 380 from leaking out thereof.

The locking unit 326 is passively biased in the locked position illustrated in FIG. 18A. In the locked position, the force exerted by the oil present in the oil chamber 380, if any, on the piston 372 is less than the force exerted by the Belleville springs 370 on the piston 372. Therefore, the resulting force is transferred to the second hemispherical portion 350b via the piston 372. The second hemispherical portion 350b moves away from the first hemispherical portion 350a and abuts at least partially against the socket casing 352a while the first hemispherical portion 350a abuts at least partially against the socket cover 352b, thereby preventing the ball 350 from moving within the socket 352 via friction and/or deformation forces. The joint mechanism 306 is then locked. Since no external intervention is required for maintaining the locking unit 326 in the locked position and locking the joint mechanism 306, the locking device 326 is passively biased in the locked position.

Upon activation of the pump, the pressure of the oil within the oil chamber 380 increases. When the force exerted by the oil contained in the oil chamber 380 on the piston 372 becomes greater than the force exerted by the spring 370 on the piston 372, the height of the oil chamber increases and the spring 370 is further compressed. The ball 350 is then free to move within the socket 352, as illustrated in FIG. 18B.

Figure 19A:
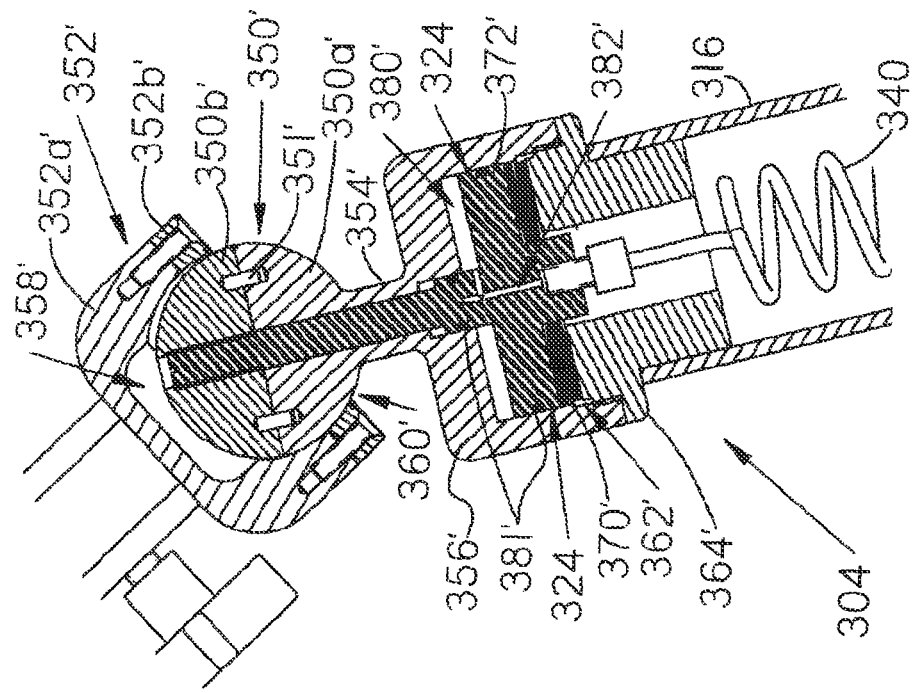
FIGS. 19A and 19B illustrate a cross-sectional view of an upper joint mechanism of the positioning apparatus of FIG. 17, in a locked and released position, respectively.
Figure 19B:
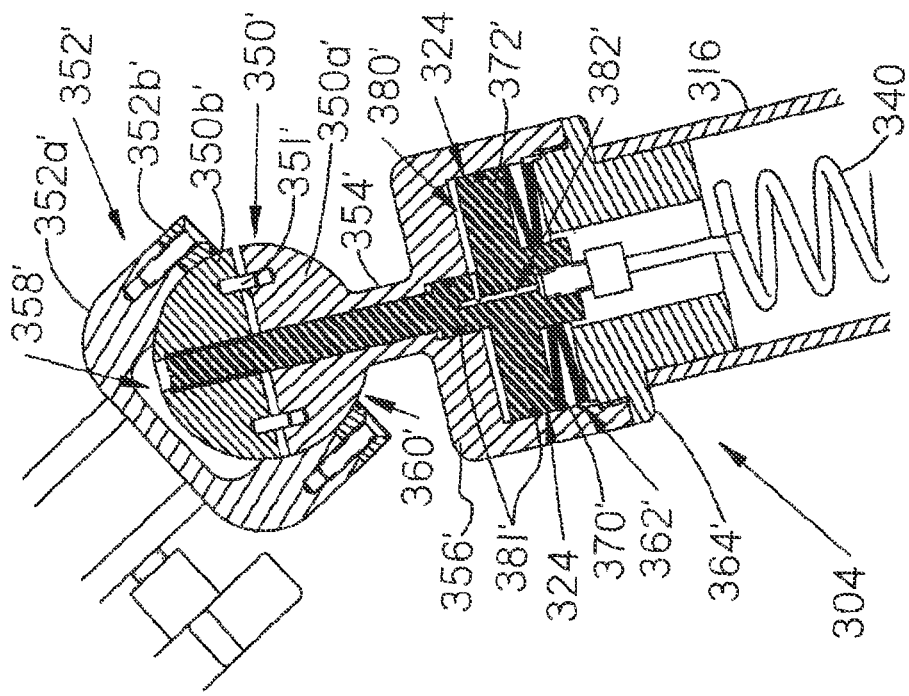

FIGS. 19A and 19B illustrate the upper joint mechanism 304 in a locked position and a released or unlocked position, respectively. The joint mechanism 304 comprises a ball 350', a socket 352', a connecting tube 354', and a casing 356'. The ball 350' comprises a first hemispherical portion 350a' fixedly secured to the casing 356' via the connecting tube 354', and a second hemispherical portion 350b' movable with respect to the first hemispherical portion 350a'. Guides 351' are used for guiding the translation of the second hemispherical portion 350b' with respect to the first hemispherical portion 350a', and preventing any rotational motion of the second hemispherical portion 350b' with respect to the first hemispherical portion 350a'. The socket 352' comprises a socket casing 352a' and a socket cover 352b'. The socket casing 352a' is provided with a recess portion 358' for receiving at least a part of the ball 350'. The socket cover 352b' is provided with an aperture 360' through which part of the ball 350' extends. The socket cover 352b' is used for enclosing the ball 350' within the socket 352', while allowing motion of the ball 350' within the socket 352'.

The casing 356' comprises a casing recess portion 362' for receiving the locking device 324 and a cover 364' for enclosing the locking device 324 within the recess portion 362'.

The locking unit 324 comprises two Belleville springs 370' and a piston 372'. The piston 372' is operatively connected to the Belleville springs 370' at one end and the second hemispherical portion 350b' at the other end. The piston receiving aperture extends through the casing 356', the connecting tube 354', and the first hemispherical portion 350a'. The piston 372' extends through the piston receiving aperture to connect the Belleville spring 370' to the second hemispherical portion 350b'. The piston 372' is used for transferring the compression force exerted by the Belleville springs 370' to the second hemispherical portion 350b'. For example, the piston 372' may abut against the second hemispherical portion 350b' for transferring the Belleville spring force thereto. In another embodiment, the piston 372' is fixedly secured to the second hemispherical portion 350b'.

The Belleville springs 370', while in compression, are enclosed between the cover 364' and the piston 372'. The cover 364' is further secured to the arm member 316 in order to secure the joint mechanism 304 thereto. A space between the piston 372' and the casing 356' defines an oil chamber 380' for receiving oil therein. The oil chamber 380' is fluidly connected to the fluidic connection 340 via an aperture 382' extending through the piston 372' and the cover 364'. Seals 381' are used for preventing the oil contained in the oil chamber 380' from leaking out thereof.

The locking unit 324 is passively biased in the locked position illustrated in FIG. 19A. In the locked position, the force exerted by the oil present in the oil chamber 380', if any, on the piston 372' is less than the force exerted by the Belleville springs 370' on the piston 372'. Therefore, the resulting force is transferred to the second hemispherical portion 350b' via the piston 372'. The second hemispherical portion 350b' moves away from the first hemispherical portion 350a' and abuts at least partially against the socket casing 352a' while the first hemispherical portion 350a' abuts at least partially against the socket cover 352b', thereby preventing the ball 350' from moving within the socket 352' via friction and/or deformation forces. The joint mechanism 304 is then locked. Since no external intervention is required for maintaining the locking device 324 in the locked position and locking the joint mechanism 304, the locking unit 324 is passively biased in the locked position.

Upon activation of the pump, the pressure of the oil within the oil chamber 380' increases. When the force exerted by the oil contained in the oil chamber 380' on the piston 372' becomes greater than the force exerted by the spring 370' on the piston 372', the height of the oil chamber 380' increases and the springs 370' are further compressed. The ball 350' is then free to move within the socket 352', as illustrated in FIG. 19B.

The operation of the locking device 328 for removably securing the arm members 316 and 318 together is similar to that of the locking unit 128 illustrated in FIGS. 16A and 16B.

While the present description refers to a three-rotational degree of freedom joint mechanism in the form of a ball and socket joint mechanism, it should be understood that any adequate joint mechanism having three rotational degrees of freedom may be used. For example, a ball joint mechanism may be replaced by three rotary joints each having a single rotational degree of freedom. The three rotary joints are connected so that their axes of rotation be orthogonal or perpendicular. The ball and socket joint mechanism may also be replaced by an ellipsoid or condyloid joint, a pivot joint, or the like.

It should also be understood that, while it has a spherical shape, the ball described in the present application may have any other adequate shape. For example, the ball may have a substantially cylindrical shape or an ellipsoidal shape as long as the socket in which the ball moves comprises a substantially spherical chamber or cavity for receiving the ball.

It should be understood that the above-described locking device which is passively biased in a locked position may be used for selectively locking any adequate joint mechanism having at least one degree of freedom and comprising at least two joint members movable the one with respect to the other.

In one embodiment, the use of a telescopic arm allows for having a suspended mass which is lower with respect to positioning apparatuses having arm members interconnected via pivots for not biasing the user's perception.

While the present description refers to upper/lower joint mechanisms having three rotational degrees of freedom, it should be understood that the joint mechanisms may each only have two degrees of freedom. In this case, the third rotational degree of freedom may be provided by the telescopic arm. For example, at least one given arm member may rotate with respect to the other arm members about an axis extending along the length of the telescopic arm. The locking device for fixing the length of the telescopic arm may also be used for locking the angular position of the given arm members with respect to the other arm members.

While the present description refers to a locking device comprising a piston and a brake pad for transferring the force exerted by an elastic/resilient member to a joint member, it should be understood that the brake pad may be omitted or integral with the piston. In this case, the piston may be in direct contact with the joint member and act as a brake pad. In another embodiment, the locking device may further comprise no piston or the piston and the brake pad may be integral with the elastic/resilient member. For example, the elastic/resilient member may be adapted to be in direct contact with the joint member and act as a paddle brake. In this case, the elastic/resilient member may be integral with the casing of the joint mechanism or be a part of the casing.

It is to be understood that the disclosure is not limited in its application to the details of construction and parts illustrated in the accompanying drawings and described hereinabove. The disclosure is capable of other embodiments and of being practiced in various ways. It is also to be understood that the phraseology or terminology used herein is for the purpose of description and not limitation.

Hence, although the present disclosure has been described hereinabove by way of illustrative embodiments thereof, it can be modified, without departing from the spirit, scope and nature of the subject disclosure.

The embodiments of the invention described above are intended to be exemplary only. The scope of the invention is therefore intended to be limited solely by the scope of the appended claims.

What is claimed is:

1. A medical positioning apparatus for positioning and holding an object, comprising:
   a telescopic member extending along a single axis extending between a first end and a second end and having an adjustable length along the single axis, wherein the telescopic member comprises a first hollow elongated member and a second hollow elongated member;
   a third hollow elongated member connected to the second hollow elongated member, wherein the second and third hollow elongated members are connected by a connector;
   a lock activation device connected to the telescopic member, wherein a fluid connection extends between the lock activation device and a T-shaped manifold within the connector;
   an interface member for receiving the object;
   a first joint mechanism movably and securing the interface member to the first end of the telescopic member;
   a second joint mechanism connected to the second end of the telescopic member;
   a base member movably connected to the second joint mechanism;
   wherein the second joint mechanism is directly rotationally connected to the base member and movably secures the base member to the second end of the telescopic member; and
   wherein the first and second joint mechanisms each having at least two rotational degrees of freedom.

2. The medical positioning apparatus of claim 1, wherein the base member comprises an elongated arm.

3. The medical positioning apparatus of claim 2, wherein the elongated arm has an end secured to the second joint mechanism and another end with an adjustable clamp.

4. The medical positioning apparatus of claim 1, wherein the first and second joint mechanisms each comprise a ball and a socket operatively connected together.

5. The medical positioning apparatus of claim 4, wherein the ball comprises a first and a second hemispherical portions moveably connected together, the first hemispherical portion being fixedly secured to the telescopic member.

6. The medical positioning apparatus of claim 1, wherein the base member extends substantially parallel to the telescopic member.

7. The medical positioning apparatus of claim 1, wherein the second hollow elongated member has a given end slidably engaged within the first hollow elongated.

8. The medical positioning apparatus of claim 1, wherein the third hollow elongated member is connected to the second joint mechanism.

9. The medical positioning apparatus of claim 1, wherein the lock activation device is a pump fluidly connected to the first and second joint mechanisms.

10. The medical positioning apparatus of claim 1, wherein the lock activation device is directly connected to the connector.

11. The medical positioning apparatus of claim 1, wherein the T-shaped manifold comprises a first outlet and second outlet.

12. The medical positioning apparatus of claim 11, wherein the first outlet is fluidly connected to a locking unit of the second joint mechanism.

13. The medical positioning apparatus of claim 11, wherein the second outlet is fluidly connected to a locking unit of the first joint mechanism.

14. The medical positioning apparatus of claim 11, wherein the first outlet is fluidly connected to a first locking unit within the third hollow elongated member and the second outlet is fluidly connected to a second locking unit within the first hollow elongated member.

* * * * *